United States Patent [19]
Sholder et al.

[11] Patent Number: 5,899,928
[45] Date of Patent: May 4, 1999

[54] DESCRIPTIVE TRANSTELEPHONIC PACING INTERVALS FOR USE BY AN EMPLANTABLE PACEMAKER

[75] Inventors: Jason A. Sholder, Beverly Hills; Kenneth Valikai, Palos Verdes Pen., both of Calif.

[73] Assignee: Pacesetter, Inc., Sylmar, Calif.

[21] Appl. No.: 08/851,922

[22] Filed: May 6, 1997

Related U.S. Application Data

[60] Provisional application No. 60/017,588, May 14, 1996.
[51] Int. Cl.$^6$ .................................................. A61N 1/362
[52] U.S. Cl. .................................. 607/27; 607/32; 607/60
[58] Field of Search ........................... 128/904; 600/510; 607/27, 32, 29, 59, 60

[56] References Cited

U.S. PATENT DOCUMENTS

| | | | |
|---|---|---|---|
| 3,774,619 | 11/1973 | Goldberg | 607/27 |
| 3,885,552 | 5/1975 | Kennedy . | |
| 4,120,307 | 10/1978 | Jirak et al. | 607/29 |
| 4,142,533 | 3/1979 | Brownlee . | |
| 4,151,513 | 4/1979 | Menken . | |
| 4,312,354 | 1/1982 | Walters | 607/27 |
| 4,332,256 | 6/1982 | Brownlee . | |
| 4,374,382 | 2/1983 | Markowitz . | |
| 4,522,208 | 6/1985 | Buffet | 607/27 |
| 4,531,527 | 7/1985 | Reinhold . | |
| 4,590,941 | 5/1986 | Saulson et al. | 607/29 |
| 4,712,555 | 12/1987 | Thornander et al. . | |
| 4,788,980 | 12/1988 | Mann et al. . | |
| 4,809,697 | 3/1989 | Causey et al. . | |
| 4,815,469 | 3/1989 | Cohen et al. . | |
| 4,884,575 | 12/1989 | Sanders . | |
| 4,940,052 | 7/1990 | Mann et al. . | |
| 4,944,298 | 7/1990 | Sholder . | |
| 4,944,299 | 7/1990 | Silvian . | |
| 5,289,824 | 3/1994 | Mills . | |

*Primary Examiner*—William E. Kamm
*Assistant Examiner*—George R. Evanisko

[57] ABSTRACT

A system and method for pulse modulating a cardiac pacing signal provides a way to have the pulse modulation characteristics be descriptive of critical information relating to the operational performance of an implanted pacemaker. The patient's ECG/EKG signal is modulated by varying the pulse-intervals of a prescribed plurality of ventricular stimulation pulses in a manner descriptive of important pacer/patient information, such as Pacemaker Battery Status, Pacemaker Sensor Function, Impedance of the Atrial Lead, Impedance of the Ventricular Lead, Existence of Specified Rhythmic Conditions, Indicated Extrsystoles Rates, and other related parameters. The resulting pulse-modulated signal is suitable for transtelephonic transmission to remote locations for subsequent demodulation and analysis. The preferred method comprises the steps of determining or measuring parametric information for selected pacemaker parameters of the implanted pacemaker, varying the pulse characteristics (i.e. timing intervals) of the ventricular stimulation pulses generated by the implanted pacemaker to be descriptive of the parametric information for the selected pacemaker parameters, and triggering the generation of a prescribed plurality of ventricular stimulation pulses having such descriptive pulse characteristics.

38 Claims, 11 Drawing Sheets

| PULSE SEGMENT | CODE | PARAMETERS | TIMING INTERVALS | | |
|---|---|---|---|---|---|
| | | | 500 MSEC | 600 MSEC | 700 MSEC |
| 1 | B | BATTERY STATUS | RRT>2 YEARS | RRT<2 YEARS | RRT<9 MONTHS |
| 2 | R | RHYTHM | NORMAL | ATRIAL TACHYCARDIA | VENTRAL TACHYCARDIA |
| 3 | A | ATRIAL LEAD IMPEDANCE | NORMAL | Z INCREASE >30% | Z DECREASE >30% |
| 4 | V | VENTRICULAR LEAD IMPEDANCE | NORMAL | Z INCREASE >30% | Z DECREASE >30% |
| 5 | E | EXTRSYSTOLES RATE | <X/MIN | >X/MIN <Y/MIN | >Y/MIN |
| 6 | S | SENSOR STATUS | NORMAL | INSENSITIVE | OVERSENSITIVE |

FIG. 4

| # | PACEMAKER CONDITION | TIMING INTERVALS ||||||
|---|---|---|---|---|---|---|---|
| | | INTERVAL #1 | INTERVAL #2 | INTERVAL #3 | INTERVAL #4 | INTERVAL #5 | INTERVAL #6 |
| 1 | PACING SYSTEM NORMAL | 600 | 600 | 600 | 600 | 600 | 600 |
| 2 | BATTERY < 9 MO RRT | 500 | 600 | 600 | 600 | 600 | 600 |
| 3 | BATTERY @ RRT | 500 | 500 | 600 | 600 | 600 | 600 |
| 4 | BATTERY @ EOL | 500 | 700 | 600 | 600 | 600 | 600 |
| 5 | BATTERY < 2 MO RRT | 700 | 600 | 600 | 600 | 600 | 600 |
| ... | ... | ... | ... | ... | ... | ... | ... |
| 28 | AUTO THRESHOLD > 25% | 600 | 600 | 600 | 500 | 600 | 600 |
| 29 | AUTO THRESHOLD > 50% | 600 | 600 | 600 | 700 | 600 | 600 |
| 30 | AUTO MODE SWITCH | 600 | 600 | 500 | 600 | 600 | 700 |
| ... | ... | ... | ... | ... | ... | ... | ... |
| 243 | ATRIAL LEAD IMP > 25% | 600 | 600 | 600 | 600 | 500 | 600 |
| 244 | VENT. LEAD IMP > 25% | 600 | 600 | 600 | 600 | 600 | 500 |
| 245 | ACTIVATED TRIGGERS | 600 | 600 | 500 | 600 | 600 | 600 |
| ... | ... | ... | ... | ... | ... | ... | ... |
| 728 | ATRIAL POLARITY REPROG | 700 | 700 | 700 | 700 | 500 | 700 |
| 729 | VENT. POLARITY REPROG | 700 | 700 | 700 | 700 | 700 | 500 |

FIG. 6

DESCRIPTIVE TRANSTELEPHONIC PACING INTERVALS FOR USE BY AN EMPLANTABLE PACEMAKER

This application claims the benefit of Provisional Application Ser. No. 60/017,588, filed May 14, 1996.

FIELD OF THE INVENTION

The present invention relates to implantable medical devices and methods, and more particularly to an implantable pacemaker that provides a method for pulse-modulating cardiac pacing signals with important pacemaker/patient information relating to the operation of the pacemaker as implanted within a given patient. The modulated cardiac pacing signals, in turn, are detectable within the patient's electrogram (EGM) or electrocardiogram (ECG) signal. The modulated EGM/ECG signal may be transtelephonically transmitted to a remote receiver located at a hospital, physician's office or other specified location, whereat the modulated information may be demodulated and analyzed.

BACKGROUND OF THE INVENTION

Modern implantable pacemakers are small, battery-powered electronic devices that are programmed to monitor the activity of the heart to determine when the heart is naturally beating, and provide stimulation pulses to atrial and/or ventricular muscle tissue of a patient's heart when the heart is not naturally beating, thereby maintaining a prescribed heart rhythm or rate. Advantageously, a pacemaker may be implanted in a patient, and coupled to the patient's heart via appropriate pacemaker leads that are also implanted. By implanting the pacemaker and leads, the pacemaker becomes an integral part of the patient, and the patient is able to maintain a substantially normal life style without the bother and worry that typically accompany the use of external (non-implanted), life-sustaining medical devices.

Nearly all implantable pacemakers in use today, as well as other implantable medical devices, can be easily monitored and configured by the attending physician in the physician's office. The process of monitoring and configuring a pacemaker is commonly referred to as "programming" the pacemakers. The programming process uses noninvasive telemetry to extract salient information which is used to customize the operation of the pacemaker to fit the individual needs of the patient. Customization is achieved by adjusting a set of "pacemaker parameters" to values that cause the pacemaker to work in an optimum way for the particular patient within whom the device has been implanted.

An important aid that is useful in monitoring the performance of an implantable pacemaker, and to facilitate the physician's understanding of the pacemaker's programmed operation as it interacts with the patient's natural cardiac activity, is the sensing and recording of various "measured parameters" relating to the pacemaker and/or patient. Unfortunately, the measured parameter information is only available to the physician or other medical personnel through a specialized programming device (typically referred to as the "programmer") which extracts the data via telemetry and displays such data in tabular and graphical formats. Thus, such pacemaker measured data becomes available only during office visits when the pacemaker can be physically interrogated by a programming device and the relevant data extracted. Such interrogation procedures, while extracting a great deal of useful information, cannot be extracted except when a patient is connected to an appropriate programming device.

Recently, a form of remote pacemaker monitoring has also been performed between scheduled office visits by the patient for the purpose of verifying the performance of the patient's implanted pacemaker. The remote pacemaker monitoring is accomplished by utilizing a variety of transtelephonic ECG transmission systems. There are a large number of transtelephonic ECG transmission systems currently available in the market. These transtelephonic ECG transmission systems are receiving widespread use because they are capable of transmitting a patients's ECG signal from his or her home or other remote location via a telephone communication system to a receiver located in a medical office, cardiac diagnostic center, or other designated facility. Advantageously, these transtelephonic ECG transmissions are sent periodically between scheduled office visits and are used to ensure that the pacemaker is performing in a satisfactory manner. If the transtelephonic monitoring detects anomalies in the ECG signal, the physician can schedule an office visit for a more detailed evaluation of the patient, and in order to make a detailed assessment of pacemaker performance, reprogram the pacemaker, or recommend surgical modifications, as required.

Disadvantageously, many transtelephonic ECG transmission systems are not configured to transmit information other than a patient's ECG. Not surprisingly, critical information other than the patient's ECG signal exists, such as the "measured parameters" that relate to the operating status of the pacemaker and/or patient, that is not readily ascertainable with an analysis of the standard ECG signal. An analysis of this other critical information could also prompt the physician to schedule an office visit for a more detailed evaluation of the patient and/or the implanted device. For example, critical patient/pacemaker information typically not available with transtelephonic ECG transmission systems, or through an analysis of the ECG signal, includes information relating to the status of the pacemaker battery, the sensitivity of the pacemaker sensors, the condition of the pacemaker leads, detected conditions relating to the patient/pacemaker such as specified rhythmic conditions, as well as other selected parameters of the implanted pacemaker.

Other related art devices and/or techniques exist for transferring pacemaker-related information from an implanted pacemaker to an external device. The most common technique involves sensing the ECG signal using an external cardiac monitoring device. Like the programming devices, or "programmers", many of these cardiac monitoring devices are designed to perform post-receipt processing and/or analysis of the ECG signal. The post-receipt processing of the ECG signal may include data compression, modulation, A–D conversion, amplification, and other well known ECG signal processing techniques.

One example of a related art system is found in U.S. Pat. No. 5,289,824, issued to Mills et ale, where there is disclosed a compact, lightweight wrist-worn cardiac data and event monitor for the recording and teletransmission of the patient's ECG data together with pacing event data. The disclosed system has prescribed circuitry which includes signal detection; data conversion, storage, display and telephonic transmitter. Event data that may be recorded along with the ECG data include time-of-day, elapsed time markers, and pulse detection markers. Both the event data as well as the ECG data are subsequently processed and analyzed in accordance with prescribed algorithms in the monitoring device.

Another example of a related art cardiac monitoring device is disclosed in U.S. Pat. No. 4,531,527, issued to Reinhold, Jr. et al., which discloses a cardiac monitoring system that detects a patient's ECG and analyzes the ECG in real time (during the patient's R—R interval). The cardiac monitoring system provides morphology analysis, heart rate data, ST segment analysis, symptomatic and asymptomatic event recordings, and the counting of ectopic runs. The analyzed data is sent over a standard voice-grade telephone line or other suitable communication channel to a central location.

Alternatively, many of the related art techniques for passing information from an implanted pacemaker to an external device involve telemetry systems. The telemetered information typically includes intracardiac data, marker data, pacing event data and other pacing related information that originates from the implanted pacemaker and is transmitted to an external device, ire., a "programmer", where the data is further processed and analyzed. Some systems adapted to accept telemetered pacing event records from the implanted pacemaker also include means for forwarding such information via telephone to a remote receiving location.

An example of such related art systems is disclosed in U.S. Pat. No. 4,142,533, issued to Brownlee et al. This patent discloses a complete system for telemetering and monitoring the functioning of an implanted pacemaker. The disclosed system specifically includes the capability for directly and simultaneously transmitting from the pacer, electrical signals indicative of pacer functions, such as, pacer rate, cell voltage, refractory period, heart rate with pacer inhibited, R-wave level and sensing margin, sensing circuit and other component failure, cardiac electrode lead break, and hermetic integrity. The telemetered signals are picked up at the patient's location for local analysis by an external programming device. Such signals, once at the programming device, may be telephonically communicated to a remote central monitoring station. (See also U.S. Pat. No. 4,332,256, issued to Brownlee et al.)

There are few known prior art systems that provide pacemaker pulse modulation, and in particular pulse-interval modulation of the ventricular stimulation pulses in order to convey information concerning the status or condition of critical pacer/patient parameters. One such system is disclosed in U.S. Pat. No. 4,312,354, issued to Walters. The '354 patent discloses an implantable pacemaker having circuit means for indicating, by pulse width modulation of the delivered pacing pulses, the programmable control states which control the selected pacemaker operating parameters. The circuitry disclosed in the '354 patent includes a parallel to serial shift register adapted to receive the control states from a pacer circuit and to generate a serial multiple bit word when the pacemaker is switched to a magnetic mode. The shift register is clocked by stimulus timing signals, and the multiple bit word drives a one shot generator, the output of which is combined with the timing pulses to produce pulse width modulated pacing pulses.

Another system known in the art is disclosed in U.S. Pat. No. 4,151,513, issued to Menken et al., which discloses an apparatus for sensing and transmitting the stimulating pulse of an implanted pacemaker over readily available, low-bandwidth transmission media to a remote receiver capable of measuring the pulse width to provide an indication of the condition of the pacemaker battery. In particular, the sensing and transmitting apparatus detects the electrical activity, e.g. the ECG, of a patient through attached electrodes and modulates a carrier or tone of a suitable frequency to be transmitted over the low-bandwidth transmission medium to the receiver, along with a pulse signal multiplied by a selected, amplification factor dependent upon the carrier frequency of the signal and the other information to be transmitted to the receiver. Typically, the patient in which the pacemaker is implanted has a transmitter for transmitting the aforementioned data to a receiver located in the doctor's office, clinic or hospital, where a regular check of the pacemaker's energy source may be made by the patient's doctor.

Neither of the systems disclosed in the '513 Menken et al. nor the '354 Walters patents provide a simple system for conveying needed information, not related to the ECG, over existing transtelephonic systems. What is needed is a simple and easy to implement technique for transtelephonically transmitting critical pacemaker/patient information to a remote facility for subsequent analysis, thus avoiding the time and expense of performing office-based examinations. The simple technique should be compatible with existing transtelephonic transmission systems, yet be able to convey information not readily ascertainable through standard ECG or intracardiac electrogram analysis.

SUMMARY OF THE INVENTION

The present invention addresses the above and other needs by providing an implanted pacemaker wherein the cardiac pacing signal is pulse modulated to convey descriptive information relating to the operational performance of the pacemaker. In particular, the present invention modulates ventricular stimulation pulses with descriptive pacer/patient information, such as Pacemaker Battery Status, Pacemaker Sensor Function, Impedance of the Atrial Lead, Impedance of the Ventricular Lead, Existence of Specified Rhythmic Conditions, Indicated Extrsystoles Rates, and other related parameters. The resulting pulse-modulated signal (i.e. ECG signal) is suitable for transtelephonic transmission to remote locations for subsequent demodulation and analysis.

In broad terms, the preferred method comprises the steps of: (a) determining or measuring parametric information for selected pacemaker parameters of the implanted pacemaker; (b) varying the pulse characteristics (i.e. timing intervals) of the ventricular stimulation pulses generated by the implanted pacemaker to be descriptive of the parametric information for the selected pacemaker parameters; and (c) triggering the generation of a prescribed plurality of ventricular stimulation pulses having such descriptive pulse characteristics. The exact form of pulse modulation of the ventricular stimulation pulses can vary substantially so long as it does not adversely affect the health and safety of the patient. However, it is preferred to keep the number and duration of the prescribed plurality of ventricular stimulation pulses (also referred to as the pulse modulated sequence) relatively short so as to minimize any interference with the normal pacing routines of the implanted pacemaker. A particularly useful feature of the present method of pulse modulating the cardiac pacing signal is to generate the prescribed plurality of ventricle stimulation pulses such that it includes one or more synchronization pulses followed by one or more descriptive pulses. The synchronization pulses identify to the recipient that the forthcoming pulses are pulse modulated descriptive pulses that are indicative of the parametric information for the selected pacemaker parameters.

In one embodiment, the method of pulse modulating the cardiac pacing signal of a patient involves the steps of: (a) determining or measuring parametric information for selected pacemaker parameters of the implanted pacemaker; (b) defining one or more descriptive pulse segments, each of the descriptive pulse segments being characterized by the occurrence of two successive pulses of the prescribed plurality of ventricular stimulation pulses; (c) associating each selected pacemaker parameter with one of the descriptive pulse segments; (d) varying the timing interval of each of the descriptive pulse segments to be indicative of the measured parametric information for the associated pacemaker parameter; and (e) generating a prescribed plurality of ventricular stimulation pulses having the descriptive timing intervals.

In another embodiment, the pulse modulation is accomplished by selecting the time intervals between each of the prescribed plurality of ventricular stimulation pulses from a set of prescribed values wherein the particular sequence or combination of prescribed values is indicative of the parametric information for one or more of the pacemaker parameters. In other words, the parametric data for a measured parameter or parameters is modulated into the entire chain of ventricular stimulation pulses by selecting prescribed time intervals for all of the descriptive pulses. The particular sequence and/or combination of all the time intervals correlates to a particular condition for one or more of the measured parameters.

The present invention may also be characterized as a cardiac pacing system that when activated or triggered by the patient provides a pulse-modulated cardiac pacing signal that is descriptive of desired or needed pacemaker information The pulse-modulated cardiac pacing signal is particularly suitable for transtelephonic transmission to receivers located at various remote locations. The cardiac pacing system includes a microprocessor-based implantable pacemaker that incorporates a means for defining the critical pacemaker parameters, a means for ascertaining or measuring parametric information relating to the critical pacemaker parameters, a means for generating ventricular stimulation pulses, a means for pulse modulating a prescribed series of ventricular stimulation pulses wherein the pulse characteristics are generally descriptive of the measured parametric information relating to the critical pacemaker parameters, and a means for activating or triggering the generation of the pulse modulated series of ventricular stimulation pulses.

Although various forms of pulse modulation can be employed within the above-described cardiac pacing system, including pulse amplitude modulation, pulse width modulation, pulse number modulation, and pulse-interval modulation, the preferred system employs a means for varying the timing intervals between successive ventricular stimulation pulses. The variations in the timing intervals between successive ventricular stimulation pulses is programmed to be descriptive of the ascertained or measured information for a particular pacemaker parameter.

Accordingly, it is an object of the present invention to provide a method for pulse modulating the patients cardiac pacing signal by varying the pulse-characteristics, and more particularly, the pulse-interval characteristics of a prescribed plurality of ventricular stimulation pulses in a manner that is descriptive of the important pacer/patient information.

A particular feature and advantage of the present system and method for pulse modulating the patient's cardiac pacing signal is that it provides a simple technique for transtelephonically transmitting important pacer/patient information to a remote facility. The pacer/patient information is modulated within a ventricular stimulation pulse train and can be easily demodulated and analyzed at the remote facility, thus avoiding the time and expense of performing office-based examinations.

Another related feature and advantage of the invention is that it provides important pacer/patient information in a form that is compatible with the tens of thousands of existing transtelephonic transmission systems currently being used by cardiac pacemaker patients.

It is an additional feature of the invention to provide a simple technique for conveying important pacer/patient information that enables a remotely located physician (or other medical personnel) to quickly and correctly comprehend the performance of the pacemaker and its interaction with the patient. If necessary, for example, the physician (or other medical personnel) can schedule an immediate office visit for a more detailed evaluation of the patient, a detailed assessment of pacemaker performance, and/or a reprogramming of the pacemaker.

BRIEF DESCRIPTION OF THE DRAWINGS

The above and other aspects, features and advantages of the present invention will be more apparent from the following more particular description thereof, presented in conjunction with the following drawings wherein:

FIG. 4 is a schematic representation of a look-up table associating a discrete timing interval for each of the selected parameters as a function of the parameter value in accordance with the preferred embodiment of the present invention;

FIG. 6 is a partial schematic representation of another look-up table associating a combination of discrete timing intervals that is descriptive of various parameters in accordance with the other embodiment of the present invention;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

To better understand how the present invention may be practiced, it will first be helpful to review the main components, and basic operation, of a pacing system. Accordingly, the following overview of a pacemaker is presented.

Figure 1:
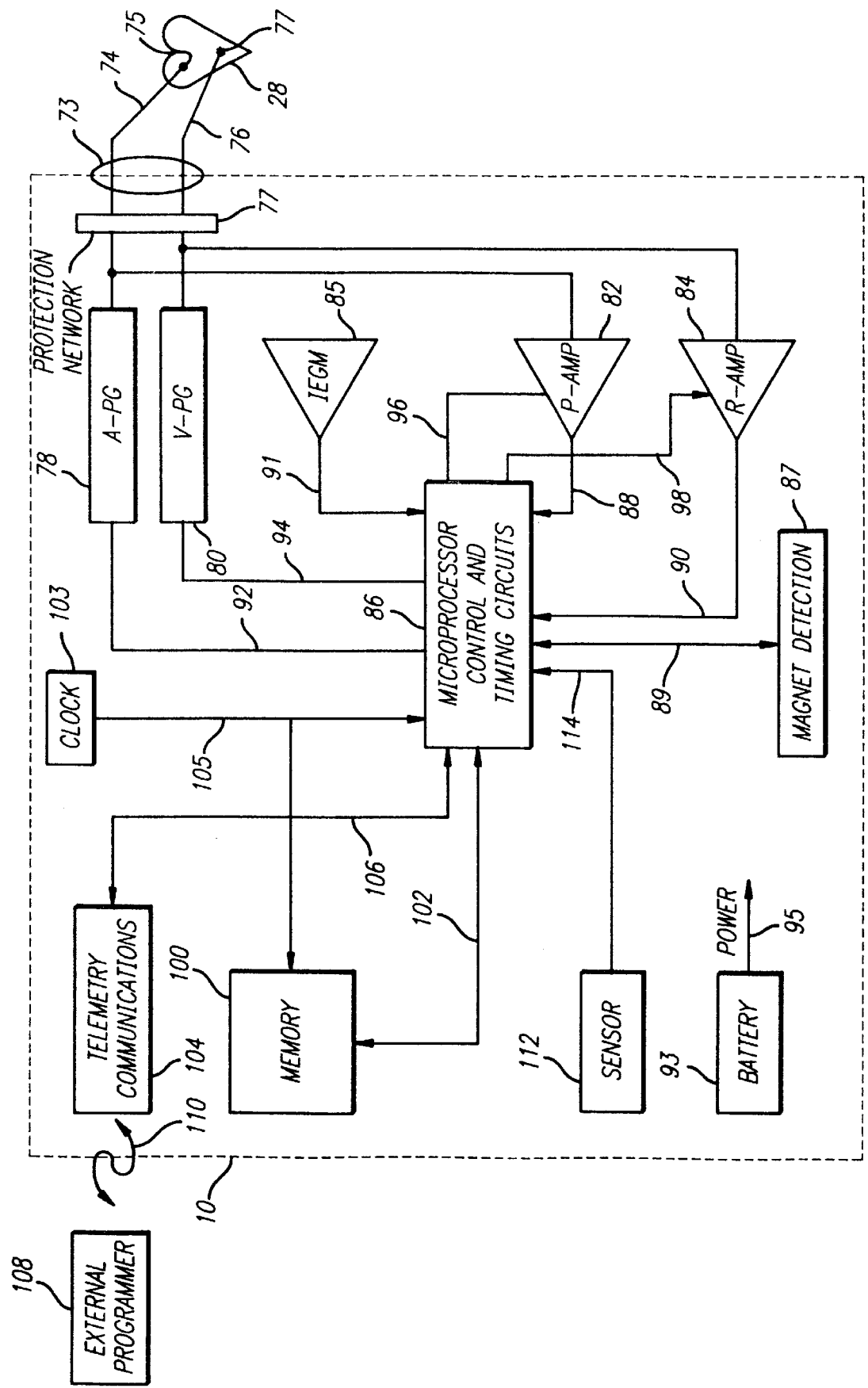
FIG. 1 is a functional block diagram of a representative multi-mode microprocessor-based implantable pacemaker that may be used with the present invention.

Turning first then to FIG. 1, a functional block diagram of a dual-chamber pacemaker 10 of a type with which the present invention may be used is shown. The pacemaker 10 is coupled to a heart 28 by way of leads 74 and 76, the lead 74 having an electrode 75 that is in contact with one of the atria of the heart, and the lead 76 having an electrode 77 that is in contact with one of the ventricles of the heart. The leads 74 and 76 are electrically and physically connected to the pacemaker 10 through a connector 73 that forms an integral part of the housing wherein the circuits of the pacemaker are housed.

The connector 73 is electrically connected to a protection network 77, which network 77 electrically protects the circuits within the pacemaker 10 from excessive shocks or voltages that could appear on the electrodes 75 and/or 77 in the event such electrodes were to come in contact with a high voltage signal, e.g., from a defibrillator shock.

The leads 74 and 76 carry stimulating pulses to the electrodes 75 and 77 from an atrial pulse generator (A-PG) 78 and a ventricular pulse generator (V-PG) 80, respectively. Further, electrical signals from the atria are carried from the electrode 75, through the lead 74, to the input terminal of an atrial channel sense amplifier (P-AMP) 82; and electrical signals from the ventricles are carried from the electrode 77, through the lead 76, to the input terminal of a ventricular channel sense amplifier (R-AMP) 84. Similarly, electrical signals from both the atria and ventricles are applied to the inputs of an IEGM (intracardiac electrogram) amplifier 85. The amplifier 85 is typically configured to detect an evoked response from the heart 28 in response to an applied stimulus, thereby aiding in the detection of "capture". (Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue).

The dual-chamber pacemaker 10 is controlled by a control system 86 that typically includes a microprocessor programmed to carry out control and timing functions. The control system 86 receives the output signals from the atrial (P-AMP) amplifier 82 over signal line 88. Similarly, the control system 86 receives the output signals from the ventricular (R-AMP) amplifier 84 over signal line 90, and the output signals from the IEGM amplifier 85 over signal line 91. These output signals are generated each time that a P-wave an R-wave, or an evoked response is sensed within the heart 28. The control system 86 also generates trigger signals that are sent to the atrial pulse generator (A-PG) 78 and the ventricular pulse generator (V-PG) 80 over signal lines 92 and 94, respectively. These trigger signals are generated each time that a stimulation pulse is to be generated by the respective pulse generator 78 or 80. The atrial trigger signal is referred to simply as the "A-trigger", and the ventricular trigger signal is referred to as the "V-trigger". During the time that either an A-pulse or V-pulse is being delivered to the heart, the corresponding amplifier, P-AMP 82 and/or R-AMP 84, is typically disabled by way of a blanking signal presented to these amplifiers from the control system over signal lines 96 and 98, respectively. This blanking action prevents the amplifiers 82 and 84 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Still referring to FIG. 1, the pacer 10 also includes a memory circuit 100 coupled to the control system 86 over a suitable data/address bus 102. This memory circuit 100 allows certain control parameters, used by the control system 86 in controlling the operation of the pacemaker, to be programmably stored and modified, as required, in order to customize the pacer's operation to suit the needs of a particular patient. Further, data sensed during the operation of the pacer may be stored in the memory 100 for later retrieval and analysis.

The memory 100 of the pacemaker 10 may take many forms, and may be subdivided into as many different memory blocks or sections (addresses) as needed in order to allow desired data and control information to be stored. A feature of the present invention is the ability to store a relatively large amount of sensed data as a data record, which data record may then be used to guide the operation of the device, e.g., whether RRT should be triggered. For example, the average battery voltage may be computed and stored on a regular basis, e.g., up to 32 times a day, with the last 120 monthly average measurements also being stored. Such information is useful for calculating longevity predictions and for time-versus-measurement graphs (generated by the external programmer). Other parameters, of course, in addition to (or in lieu of) battery voltage, may be similarly sensed, stored, averaged (or otherwise processed), and then used for comparison purposes, such as battery current, battery impedance, etc. Advantageously, modern memory devices allow for the storage of large amounts of data in this manner.

A clock circuit 103 directs an appropriate clock signal(s) to the control system 86, as well as to any other needed circuits throughout the pacemaker 10 (e.g., to the memory 100) by way of clock bus 105.

A telemetry/communications circuit 104 is further included in the pacer 100 This telemetry circuit 104 is connected to the control system 86 by way of a suitable command/data bus 106. In turn, the telemetry circuit 104, which is included within the implantable pacer 10, may be selectively coupled to an external programming device 108 by means of an appropriate communication link 110, which communication link 110 may be any suitable electromagnetic link, such as an RF (radio frequency) channel, a magnetic link, an inductive link, an optical link, and the like. Advantageously, through the external programmer 108 and the communication link 110, desired commands may be sent to the control system 86. Similarly, through this communication link 110 and the programmer 108, data (either held within the control system 86, as in a data latch, or stored within the memory 100) may be remotely received from the pacer 10 In this manner, non-invasive communications can be established with the implanted pacer 10 from a remote, non-implanted, location.

The pacer 10 additionally includes a battery 93 which provides operating power to all of the circuits of the pacer 70 via a POWER signal line 95. The voltage of the pacemaker battery 93 on the POWER signal line 95 is monitored by appropriate monitoring circuits within the control system 86, or elsewhere within the pacemaker 10, in order to ascertain whether the battery voltage has dropped below a predefined recommended replacement time (RRT) threshold. If so, as explained more fully below, then an RRT mode is invoked wherein the basic pacing interval of the pacemaker is increased (i.e., the basic pacing rate is slowed down). The manner in which this RRT mode is triggered is the subject of the present invention.

It is noted that the pacer 10 in FIG. 1 is referred to as a dual-chamber pacemaker because it interfaces with both the atria and the ventricles of the heart. Those portions of the pacer 10 that interface with the atria, e.g., the lead 74, the P-wave sense amplifier 82, the A-PG 78, and corresponding portions of the control system 86, are commonly referred to as the "atrial channel". Similarly, those portions of the pacer 10 that interface with the ventricles, e.g., the lead 76, the R-wave sense amplifier 84, the V-pulse generator 80, and corresponding portions of the control system 86, are commonly referred to as the "ventricular channel".

As needed for rate-responsive applications, the pacemaker 10 further includes at least one sensor 112 that is connected to the control system 86 of the pacer 10 over a suitable connection line 114. While this sensor 112 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, that is mounted to the case of the pacemaker. Other types of sensors are also known, such as sensors that sense the oxygen content of blood, respiration rate, ph of blood, body motion, and the like. The type of sensor used is not critical to the present invention. Any sensor capable of sensing a parameter relatable to the rate at which the heart should be beating can be used. Such sensors are used with "rate-responsive" pacemakers in order to adjust the basic rate (pacing cycle) of the pacer in a manner that tracks the physiological needs of the patient. To this end, the control system 86 (when operating in a rate-responsive mode) receives output-signals from the sensor 112 and converts them to a sensor-indicated-rate (SIR) signal which is used by the control system 86 to set the pacing interval of the pacemaker.

The pacemaker 10 further includes magnet detection circuitry 87, coupled to the control system 86 over signal line 89. It is the purpose of the magnet detection circuitry 87 to detect when a magnet is placed over the pacemaker, which magnet may be used by a physician or other medical personnel to perform various reset functions of the pacemaker 10, and/or to signal the control system 86 that an external programmer 108 is in place to receive data from, or send data to, the pacemaker memory 100 or control system 86 through the telemetry communications circuits 104.

The telemetry or communications circuit 104 may be of conventional design, such as is described in U.S. Pat. No. 4,944,299, or as is otherwise known in the art. Similarly, the external programmer 108 may be of any suitable design known in the art, such as is described in U.S. Pat. No. 4,809,697. Likewise, the memory circuit 100, and the circuits utilized in the atrial and ventricular channels may all be of common design as is known in the pacing art.

The control system 86 may be realized using a variety of different techniques and/or circuits. The preferred type of control system 86 is a microprocessor-based control system, as described below in conjunction with FIGS. 8–11. It is noted, however, that the control system 86 could also be realized using a state machine. Indeed, any type of control circuit or system could be employed for the control system 86. The present invention is not concerned with the details of the control system 26. Rather, it is concerned with the end result achieved by the control system, particularly relative to how the control system 86 controls or modulates the ventricular stimulation pulses, when triggered, in order to convey information about the status and operation of the pacemaker through conventional ECG monitoring channels. Those of skill in the implantable medical device art, given the teachings presented herein, should thus be able to fashion numerous different types of control systems or circuits that achieve the desired stimulus pulse modulation.

Representative of the types of control systems that could be used with the invention is the microprocessor-based control system described in U.S. Pat. No. 4,940,052, entitled "Microprocessor Controlled Rate-Responsive Pacemaker Having Automatic Rate Response Threshold Adjustment". Reference is also made to U.S. Pat. Nos. 4,712,555 and 4,944,298, wherein a state-machine type of operation for a pacemaker is described; and U.S. Pat. No. 4,788,980, wherein the various timing intervals used within the pacemaker and their inter-relationship are more thoroughly described. The '052, '555, '298 and '980 patents are all incorporated herein by reference.

Additional details relative to a particular multi-mode, microprocessor-based, pacemaker that may be utilized in order to implement the present invention are presented below in conjunction with FIGS. 8–11. However, as indicated above, the present invention is not limited by a particular pacemaker design, but may be implemented using any pacemaker design wherein operating parameters of the pacemaker and/or the patient/pacemaker interface may be monitored, measured, and stored, and wherein the pattern of ventricular stimuli may be modulated in the manner described herein. Hence, a description of the type of pulse modulation contemplated by the present invention, including the type of information that may be included in such modulation, as well as the manner in which such modulation is implemented, will next be described.

Figure 2A:
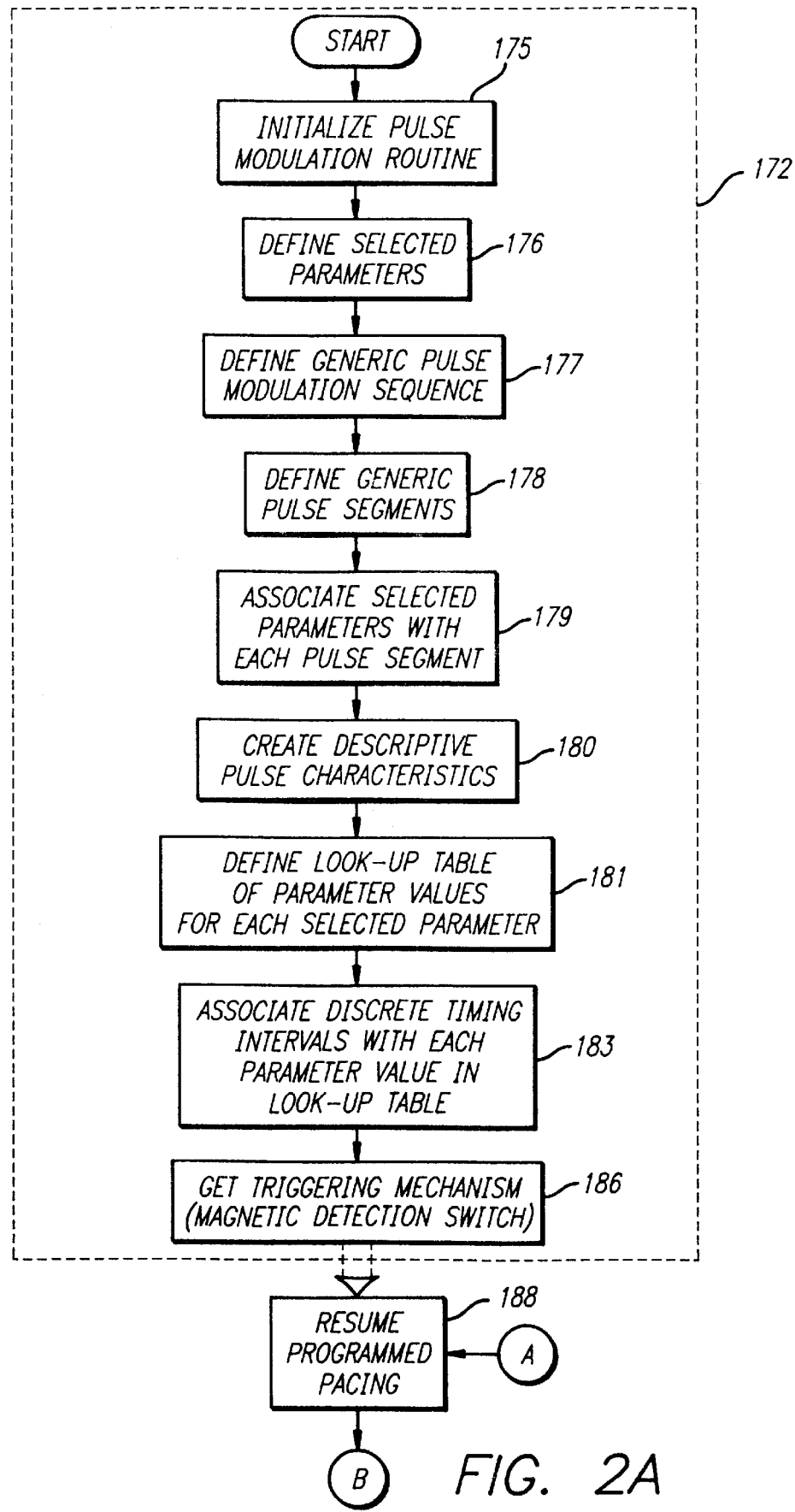
FIGS. 2A and 2B show a flowchart of a method for pulse modulating a cardiac pacing signal with descriptive information relating to the operational performance of an implanted pacemaker.
Figure 2B:
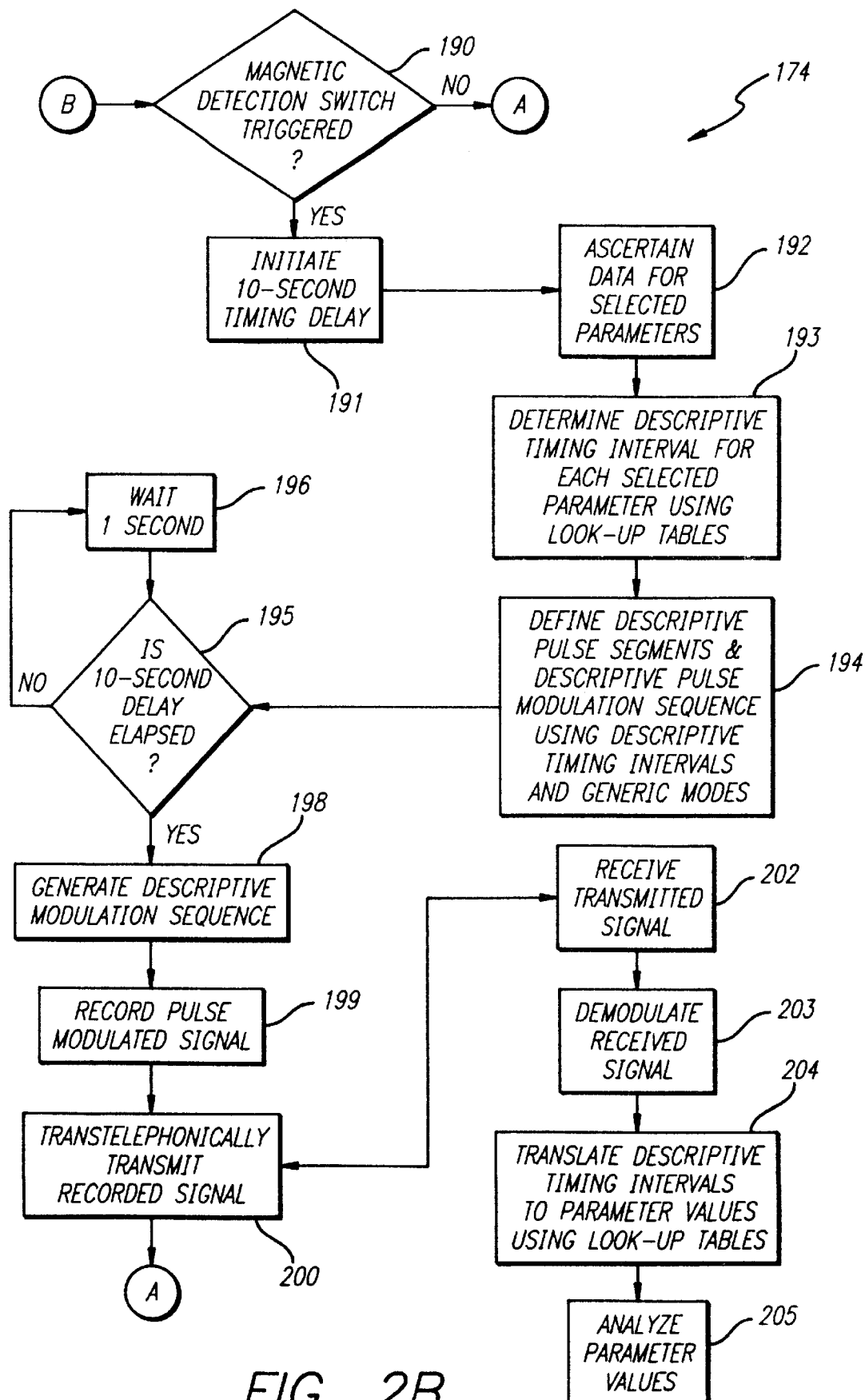

One method that may be used to implement the pulse modulation of the invention is depicted in the flowchart of FIGS. 2A and 2B. Each of the particular steps of the method is represented by an individual block in FIGS. 2A and 2B, each of which has a reference numeral associated therewith. The same method is depicted in both FIGS. 2A and 2B, so reference is made to both figures collectively as though they were a large single sheet. As seen in FIGS. 2A and 2B, the method is bifurcated into a programming phase 172 (FIG. 2A) and an operational phase 174 (FIG. 2B). The programming phase 172 involves the initial programming or reprogramming of the microprocessor-based pacemaker with a particular pulse modulation routine. This programming phase preferably involves three primary steps including: (1) initialization of the Pulse Modulation Routine (block 175); (2) creation of descriptive pulse characteristics (block 180); and (3) enabling or setting of a triggering mechanism (block 186).

More specifically, the step of initializing the pulse modulation (block 175) involves a first substep of defining a plurality of selected parameters (block 176), the selected parameters relating to critical pacemaker and/or patient information. The second substep defines a generic pulse modulation sequence of sufficient length and duration to contain the critical information relating to the selected parameters (block 177). This defined pulse modulation sequence model must also be formed such that the patient's natural cardiac activity will not interfere with the modulation sequence and that when invoked the modulation sequence does not cause harm to the patient or place the patient at unnecessary risk. Optionally, the generic pulse modulated sequence model can be further defined as a plurality of pulse segments (block 178), each pulse segment preferably representing two successive pulses. The final substep in the initialization of the pulse modulation routine involves associating the selected parameters with the defined pulse segments (block 179). In the preferred embodiments each of the selected parameters is associated with at least one pulse segment such that the information relating to that parameter can be extracted by analyzing the associated pulse segments.

The step of creating descriptive pulse characteristics (block 180) further comprises the substeps of defining or creating look-up tables for each selected parameter (block 181). The look-up tables preferably include a short listing of acceptable parameter values or ranges of parameter values for the particular parameter. Associated with each parameter value or range of values is a prescribed timing interval (block 183). The look-up tables and data included therewith (i.e. parameter values/ranges and associated timing intervals) are preferably stored in the pacemaker memory and can be easily retrieved and incorporated into the generic pulse segment and pulse modulation sequence models upon activation by the patient.

The final step in the programming phase of the present method involves enabling or setting a triggering mechanism (block 186). The preferred triggering mechanism is for the patient to place a magnet over his or her chest in order to activate the magnetic detection switch or reed switch 87, the use of which is commonly known in the art. Typically, placement of the magnet will also involve placement of a suitable transducer capable of sensing the patient's EGM or ECG and transtelephonically sending such sensed EGM or ECG to a remote location. (Note that "ECG" usually refers to the patient's electrogram signal as sensed by the pacemaker leads and sensing circuits; whereas "EKG" refers to the patient's electrocardiogram, sensed using external electrodes placed at various locations on the patient's skin.

After the programming phase 172 is completed, the pacemaker resumes it's primary function of pacing the patient's heart in accordance with a selected pacemaker operating mode and/or pacing algorithm (block 188). Advantageously, the present invention may be used with a wide variety of different pacemakers and pacemaker operating modes, the details of which operating modes and/or pacing algorithms are not particularly relevant to the invention. The selected pacing function continues (at block 188) until the magnetic detection switch is triggered (block 190) which action invokes the operational phase of the present method. During the operational phase 174, a pulse-modulated cardiac pacing signal is produced that is descriptive of critical or important pacemaker information. The operational phase 174 involves the essential steps of: (1) activating the triggering mechanism (block 190); (2) ascertaining the measured values of the selected parameters (block 192); (3) determining a descriptive pulse modulation sequence that is generally representative of the measured values of the selected parameters (block 194); and (4) generating a plurality of stimulation pulses in accordance with the determined pulse modulation sequence (block 198).

A preferred technique for activation involves the placement and subsequent removal of a magnet (block 190) over the implanted pacemaker which activates the magnetic detection switch 87 (FIG. 1). As shown in FIG. 2B, upon activation of the magnetic detection switch, the preferred operational phase initiates a ten second delay (block 191) which allows the patient sufficient time to put down the magnet and hook up a suitable transtelephonic transmission system. During the ten second delay, the programmed pacemaker proceeds to ascertain or determine the salient information for the selected parameters that is to be conveyed (block 192). The data for the selected parameters can be obtained through direct measurement, retrieval from pacemaker memory, estimation algorithms, or other suitable means. Once the data are ascertained, the next step is to determine a descriptive timing interval for each selected parameter corresponding to the data using various look up tables (block 193)(See e.g. FIG. 4). Having determined the plurality of descriptive pulse intervals, the next step involves defining a plurality of descriptive pulse segments and a descriptive pulse modulation sequence using the descriptive timing intervals provided from the look-up tables and the generic models (block 194) defined in the programming phase 172.

Figure 3:
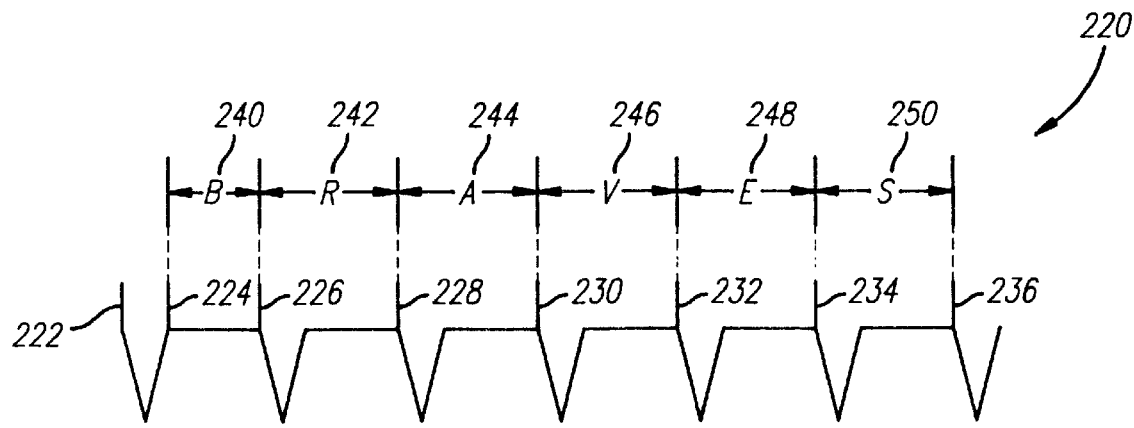
FIG. 3 depicts the type of pulse-interval modulated waveform that is produced in accordance with one embodiment of the present invention.

As soon as the ten second delay elapses (blocks 195 and 196), the programmed pacemaker proceeds to generate a plurality of ventricular stimulation pulses wherein the timing interval between pulses is modulated in accordance with the defined descriptive pulse modulation sequence (block 198). In the preferred embodiment, the pacemaker would deliver eight ventricular stimulation pulses as shown in FIG. 3. The first two pulses are identification pulses which are followed by six descriptive pulses. The plurality of pacing pulses (both identification and descriptive pulses) are of sufficient magnitude to cause capture of the patient's heart and are readily detectable by transtelephonic transmitters which then forward the pulse-interval modulated cardiac pacing signal via the telephone line or other connection to a remote receiver.

More particularly, the cardiac signal resulting from the pulse-interval modulated ventricular stimulation pulses may be recorded as an electro cardiogram (ECG) signal (block 199). The recorded pulse modulated ECG signal may then be transtelephonically transmitted to a remote location (block 200) such process being well known in the art. At the remote location, the transmitted signal is received (block 202) and subsequently demodulated (block 203). The descriptive timing intervals extracted from the pulse modulated ECG signal are then translated back to the selected parameter data using another look-up table (block 204) which facilitates the further analysis of the selected parameter data by medical personnel at the remote facility (block 205).

Turning now to FIG. 3, which illustrates a representative pulse-interval modulated waveform 220 that is produced in accordance with the invention, it can be seen that the first two identification pulses 222, 224 are preferably separated by a pulse interval of only about 100 milliseconds (ms). Since the first identification pulse 222 is of sufficient magnitude and duration to cause ventricular capture, the second identification pulse 224 (100 ms later) occurs during the physiological refractory period and has no effect on the patient. These two rapid identification pulses do, however, allow the recipient to know that the six descriptive pulses will immediately follow. The six descriptive pulses 226, 228, 230, 232, 234, and 236 are separated from each other (i.e, have prescribed timing intervals associated therewith) of either 500 ms, 600 ms or 700 ms, with the timing interval for each segment having been programmably determined by the microprocessor subassembly to be descriptive of the status or condition of the identified pacer/patient information.

By way of example, the invention may utilize six descriptive time intervals (also referred to as "pulse segments") 240, 242, 244, 246, 248, and 250 to describe the general status of six identified parameters. These six general status parameters respectively include: an indication of the battery status (B), segment 240; notification of recent tachycardia conditions in the patient (R), segment 242; condition of the atrial lead (A), segment 244; condition of the ventricular lead (V), segment 246; the measured extrsystoles rate of the patient (E)e segment 248; and an indication of the physiological sensor status (S), segment 250.

In the presently disclosed embodiment, the first descriptive pulse segment 240, defined as the interval between the last identification ventricular pulse 224 and the first descriptive ventricular pulse 226, is indicative of the status of the implantable pacemaker battery. The second descriptive pulse segment 242 is defined as the interval between the first descriptive ventricular pulse 226 and the second descriptive ventricular pulse 228. The second descriptive pulse segment 242 indicates whether any tachycardia conditions have been detected recently. The third descriptive pulse segment 244 (the interval between the second and third descriptive ventricular pulses) and the fourth descriptive pulse segment 246 (the interval between the third and fourth descriptive ventricular pulses) provides information relating to the atrial and ventricular leads, respectively.

The fifth descriptive pulse segment 248 is defined as the interval between the fourth descriptive ventricular stimulation pulse 232 and the fifth descriptive ventricular stimulation pulse 234. The fifth descriptive pulse segment 248 provides an indication of the measured extrsystoles rate in the patient. The sixth descriptive pulse segment 250 is defined as the interval between the fifth descriptive ventricular stimulation pulse 234 and the sixth descriptive ventricular stimulation pulse 236 and is generally indicative of the physiological sensor status. The look-up table associated with the six parameters is shown in FIG. 6.

For each of the parameters identified in FIG. 6, the process of ascertaining the parameter values and associating a discrete timing interval varies. For example, the indication of the battery status "B" is determined by measuring the battery voltage and battery current and then determining the battery impedance. An analysis of the battery impedance provides an estimate of the time remaining until the pacemaker reaches it's recommended replacement time (RRT). If the recommended replacement time (RRT) for the pacemaker is greater than a prescribed upper reference value (i.e. two years), then a timing interval of 500 ms is set for the first pulse segment 240. If the recommended replacement time (RRT) for the pacemaker is less than a prescribed lower reference value (i.e. nine months), then a timing interval of 700 ms is set for the first pulse segment 240. Finally, a timing interval of 600 ms indicates that the recommended time for pacemaker replacement is, for example, between the upper reference and lower reference values (i.e. between nine months and two years).

The second parameter "R" relates to the presence of any tachycardia conditions. A determination of whether any tachycardia conditions have been recently detected is simply done by retrieving such information from the memory unit 100 of the pacemaker 10 (FIG. 1). In the preferred pacemaker, the pacemaker comprises a microprocessor-controlled pacemaker and the microprocessor executes various algorithms that continually assess cardiac signals to detect and record the occurrence of any tachycardia conditions. A timing interval of 500 ms indicates that there were no tachycardia conditions detected and recorded within a prescribed time frame. A timing interval of 600 ms indicates that one or more atrial tachycardia conditions were detected and recorded with no ventricular tachycardia conditions detected within the prescribed time frame. Lastly, a timing interval of 700 ms indicates that the pacemaker recently detected and recorded a ventricular tachycardia condition in the patient within the prescribed time frame.

The third pulse segment 244 or the "A" segment, and the fourth pulse segment 246, or the "V" segment, relate to the general condition of the atrial and ventricular leads, respectively. The general condition of the leads is determined by ascertaining the atrial lead impedance (corresponding to the third pulse segment 244), and the ventricular lead impedance (corresponding to the fourth pulse segment 246). Atrial lead impedance can easily be determined by measuring the pulse voltage and pulse current on the atrial channel; while the ventricular lead impedance can easily be determined by measuring the pulse voltage and pulse current on the ventricular channel. If the impedance of each of the respective leads is normal (i.e. 500 ohms) or within a prescribed range (i.e. 350–650 ohms), the timing interval for the respective pulse segment is set at 500 ms. If the impedance of each of the respective leads has increased more than 30% above normal value (i.e. >650 ohms), then the respective timing interval is set at 600 ms. Conversely, if the impedance of each of the respective leads has decreased more than 30% below normal value (i.e. <350 ohms), then the timing interval for the corresponding pulse segment is set at 700 ms.

The fifth pulse segment 248, or the "E" segment, relates to the measured extrsystoles rate of the patient. Again, the pacemaker is designed to continually detect and record premature ventricular events (PVEs) through the execution of various detection algorithms. In particular, a count of the total number of PVEs is maintained within the memory 100 of the pacemaker 10 (FIG. 1) which can be interrogated and periodically cleared. The date and time of the last clearing of the PVE data is also stored in the memory of the pacemaker. When ascertaining the extrsystoles rate information, the PVE data and corresponding date/time stamp are retrieved from the pacemaker memory. The extrsystoles rate, which is expressed in events per minute, is then calculated by taking the total number of PVEs and dividing by the number of minutes that have elapsed since the recorded date/time stamp. If the average measured extrsystoles rate in the patient is less than or equal to a prescribed extrsystoles lower reference values then a timing interval of 500 ms is set for the fifth pulse segment. If the average measured extrsystoles rate for the patient is greater than or equal to a prescribed extrsystoles upper reference value, then a timing interval of 700 ms is set for the fifth pulse segment. Finally, a timing interval of 600 ms for the fifth "E" segment 248 indicates that the average measured extrsystoles rate in the patient is between the extrsystoles upper reference value and the extrsystoles lower reference value. The actual values used for the upper reference value and lower reference value are programmable values that may be set by the physician or other medical personnel depending upon the particular patient. (PVEs are a more common occurrence for some patients than for others).

The sixth pulse segment 250, or the "S" segment, is generally descriptive of the physiological sensor status. The sensor status is determined by comparing the average Sensor Indicated Rate (SIR) expressed in pulses per minute to prescribed reference values. In the preferred embodiment, the pacemaker 10 provides for data storage of the SIR over time and can be cleared periodically. When cleared, the date and time of the clearing is retained in the pacemaker memory. If the average SIR over a given period of time is below a prescribed lower SIR reference value, the sensor is considered insensitive and the timing interval for the sixth pacing segment is set to 600 ms. However, if the average Sensor Indicated Rate exceeds a prescribed upper SIR reference value, the sensor is deemed to be oversensitive and the timing interval for the sixth pacing segment is set to 700 ms. If neither of the above SIR comparisons dictate the timing interval, the condition of the sensor is identified as normal and the timing interval for the sixth pacing segment is set to 500 ms.

After each of the six parameters have been ascertained and the respective timing intervals set for each pulse segment "B", "R", "A", "V", "E", and "S", the pacemaker generates a train of ventricular stimulation pulses having the descriptive timing intervals identified above.

Advantageously, the various criteria and reference values associated with each of the descriptive pulse intervals can be specifically tailored for each patient. In the present embodiment, the parameter criteria and reference values associated with the 600 ms and 700 ms timing intervals can be programmed by the physician in accordance with his or her preferences and/or the history of the patient. Moreover, while the present embodiment teaches the use of six descriptive pulses thereby providing general status information of six pacer/patient parameters identified above, it is contemplated that additional (or fewer) parameters and descriptive pulses can be incorporated, as needed.

Still further, it is noted that the above-described embodiment of the invention utilizes three discrete timing intervals (500, 600 and 700 ms) identifying three different conditions for each parameter as identified in FIG. 6. However, the present invention can be easily modified to utilize a different number of discrete timing intervals. For example, a system employing two descriptive time intervals can be used to convey information on a go/no-go basis. In other words, the measured parameter is either within specification tolerance limits or is not within prescribed limits thus identifying a potential problem. On the other hand, a system employing five descriptive timing intervals may include allowable settings of 500, 550, 600, 650, and 700 ms in order to convey more detailed information with respect to each parameter.

The important aspects which govern the selection of permissible timing intervals also relate to the safe operation of the pacemaker in the patient. For example, the selected timing intervals should not be so fast as to cause tachycardiac conditions within the patient However, it is possible, and to some extent preferable, to take full advantage of the physiological refractory period immediately following ventricular stimulation of the heart. Any pulses generated during this refractory window have little or no effect on the health and safety of the cardiac patient. In addition, the selected timing intervals should not be too slow which could adversely affect the pacing condition of the patient. Further, the selected timing intervals should be fast enough to ensure reasonably safe overdrive pacing which prevents natural cardiac rhythm from contaminating the pulse modulated signal.

Figure 5:
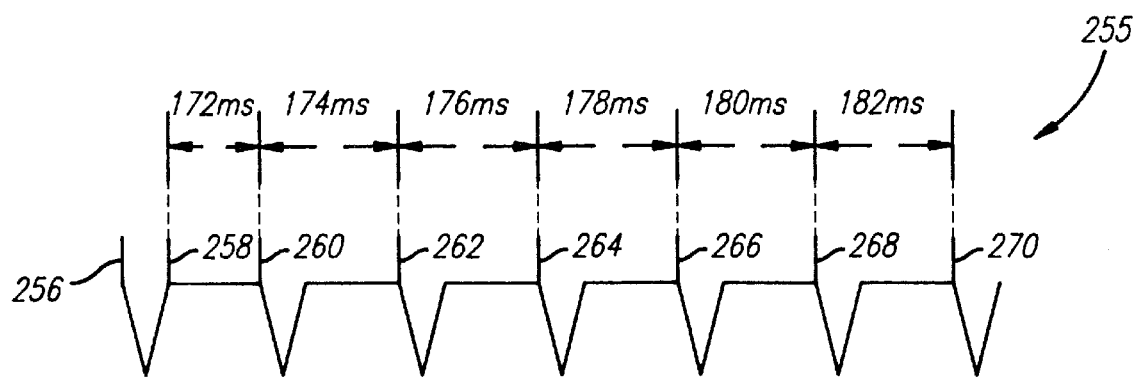
FIG. 5 depicts the type of pulse-interval modulated waveform that is produced in accordance with another embodiment of the present invention.

An alternative embodiment of the invention utilizes a pulse-interval modulating technique that utilizes a plurality of pulse segments within a defined pulse modulation sequence that collectively provides an indication of one or more parameters, as shown in FIGS. 5 and 6. In many respects, this alternative embodiment is very similar to the previously discussed embodiment in that it is a programmable pulse-interval modulating process. With this in mind, the following discussion focuses on the differences between the two embodiments rather than repeat a complete description of the entire process.

In the first embodiment, the pulse modulation sequence was defined around six selected parameters and six descriptive pulse segments with each parameter associated with a particular descriptive pulse segment. There were also three discrete timing intervals (500, 600, and 700 ms) allowable for each pulse segment. The timing interval selected for each pulse segment is descriptive of information relating to a particular parameter. Thus the complete pulse modulated signal conveyed six pieces of information from a composite of eighteen (18) possible choices. In the alternative embodiment of FIGS. 5 and 6, two identification pulses 256 and 257, followed by six descriptive pulses 260, 262, 264, 266, 268, and 270, which define six descriptive pulse segments 272, 274, 276, 278, 280, and 282, are also employed. However, the information conveyed by the sequence and arrangement of pulses for the alternative embodiment must be considered collectively. As with the earlier described embodiment, the discrete timing interval for each descriptive pulse segment 272, 274, 276, 278, 280, and 282 is selected from a group of three choices (i.e. 500, 600, and 700 ms). The information contained within the composite pulse modulation sequence, however, is not limited to the six parameters but rather may be indicative of any number of selected parameters. In this alternative embodiment, there are $X^n$ possible combinations of timing intervals, where X is the number of timing interval selections, and n is the number of descriptive pulse segments included within the pulse modulated sequence. The waveform 255 represented in FIG. 5, for example, would yield $3^6$ or 729 different possible combinations of timing intervals. Each of these possible combinations are included in a look-up table, which is partially depicted in FIG. 6. The 729 different combinations can be programmed to provide information about one parameter, two parameters, five parameters, ten parameters, etc.

Although the present invention is described with reference to a pair of specific embodiments, it is contemplated that alternative pulse modulating techniques can also be utilized with the invention. Thus, in lieu of the preferred pulse-interval modulation techniques, it may also be possible to utilize pulse amplitude modulation, pulse width modulation, and pulse number modulation techniques. It is important, however, to provide a recording or monitoring system that is capable of distinguishing the modulated attributes of the generated waveform. Since many transtelephonic transmission systems are adapted to use standard ECG signals measured externally to the patient, the preferred modulation technique is pulse-interval modulation, as described above in connections with FIGS. 3–6. This is because the externally measured ECG signal is often subject to fluctuations in the measured amplitude and width of the sensed pulses due primarily to the placement of the skin electrodes, general condition of the patient and other variables. Thus, pulse-interval modulation of the externally measured ECG signal is believed to be the easiest form of modulation that can be accurately demodulated and the most reliable form of pulse modulation that can be used with implantable pacemakers.

Figure 7A:
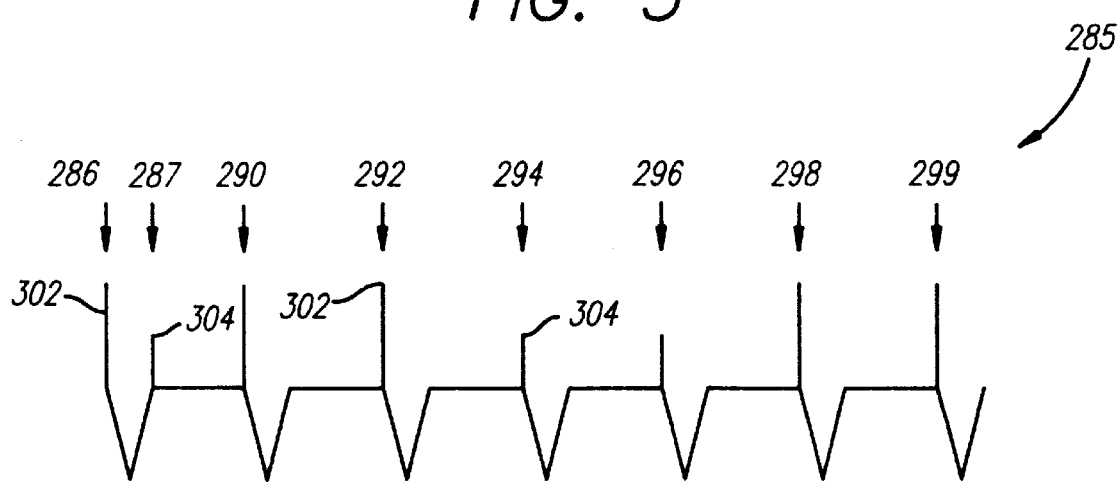
FIGS. 7A, 7B, and 7C depict several alternative pulse modulated waveforms that can be produced in accordance with other embodiments of the present invention.
Figure 7B:
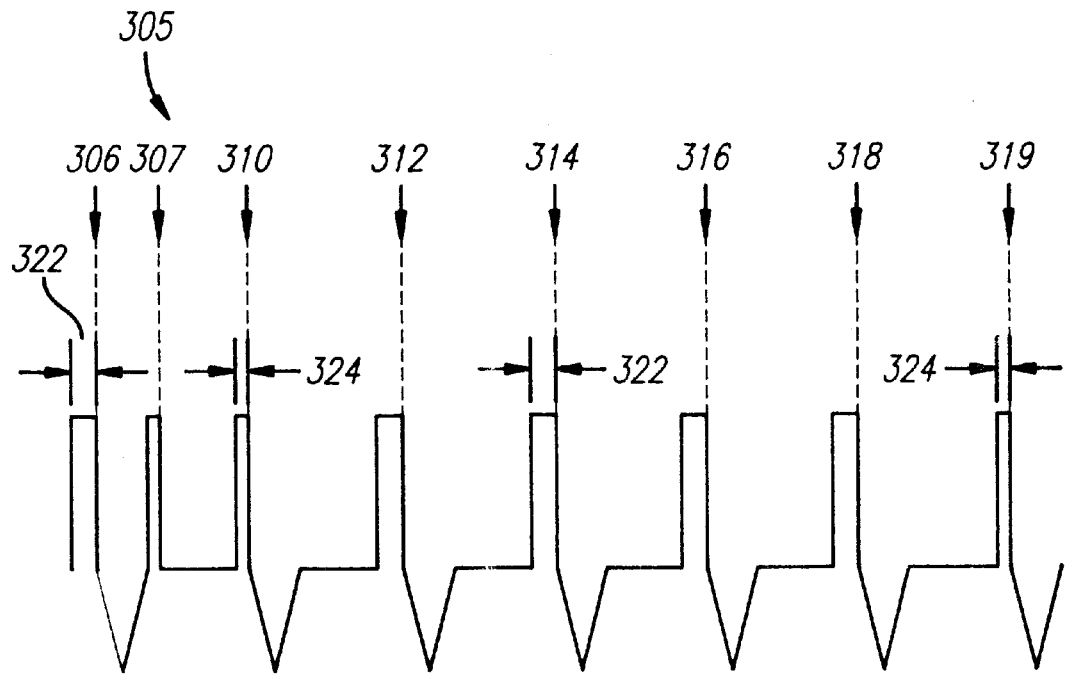
Figure 7C:
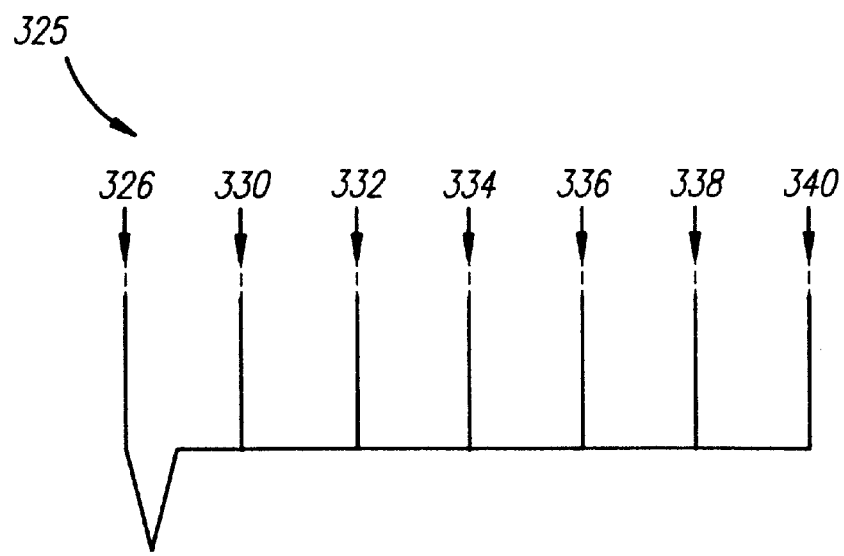

Turning next to FIGS. 7A, 7B and 7C, there are shown several alternative pulse modulated waveforms that could be produced in accordance with other embodiments of the present invention. FIG. 7A represents an example of a pulse amplitude modulated waveform 285 having six descriptive pulses 290, 292, 294, 296, 298, and 299. Each of the descriptive pulses 290, 292, 294, 296, 298, and 299 may exhibit one of two selected amplitudes. A sufficiently high amplitude 302 (i.e. 4.0 Volts) may indicate that the parameter associated with that particular pulse is within normal or acceptable limits. A low amplitude 304 (i.e. 2.0 Volts), on the other hand, may indicate that there is some type of anomaly associated with the parameter which requires further examination. Such pulse amplitude modulated waveform 285 also includes a pair of amplitude reference pulses 286 and 287 which are followed by the six descriptive pulses 290, 292, 294, 296, 298, and 299. The amplitude reference pulses 286, 287 identify to the recipient that the next six pulses are pulse amplitude modulated descriptive pulses that are indicative of the parametric information for the selected pacemaker parameters. In addition, the amplitude of the first amplitude reference pulse 286 might be indicative of the high amplitude pulse 302. The amplitude of the second amplitude reference pulse 287 might be indicative of the low amplitude pulse 304. The reference amplitudes are of importance to the recipient of the modulated signal because the measured or recorded signal is often subject to fluctuations in amplitude. Thus, the absolute amplitude need not be accurate, so long as one can distinguish between a high amplitude pulse and a low amplitude pulse.

Similarly, FIG. 7B represents a representation of a pulse width modulated waveform 305 having six descriptive pulses 309, 312, 314, 316, 318, and 319. Each of the descriptive pulses 309, 312, 314, 316, 318, and 319 may exhibit, for example one of two selected pulse widths. A sufficiently wide pulse width 322 (i.e. 0.6 ms) may indicate that the parameter associated with that particular pulse is within acceptable limits. A descriptive pulse having a relatively narrow width 324 (i.e. 0.2 ms) may indicate that there is some type of anomaly associated with the parameter which requires the physician to schedule an office visit. As with the suggested pulse amplitude modulated waveform, the suggested pulse-width modulated waveform 305 would include a pair of pulse width reference pulses 306 and 307 which are then followed by the six or more descriptive pulses 309, 312, 314, 316, 318, and 319. The pulse width reference pulses 306, 307 not only identify to the recipient that the next six pulses are the modulated descriptive pulses, but they also provide the references against which the pulse width of the descriptive pulses 309, 312, 314, 316, 318, and 319 are compared. For example, the pulse width of the first reference pulse 306 might be indicative of the wide pulse 322 whereas the pulse width of the second reference pulse 307 might be indicative of the narrow width pulse 324.

Finally, FIG. 7C represents a pulse number modulated waveform 325 that may be incorporated within the invention. Basically, the pulse-number modulation scheme utilizes six descriptive pulses 330, 332, 334, 336, 338, and 340 separated by about 15 ms during the physiological refractory period immediately after an identification pulse 326. As before each descriptive pulse 330, 332, 334, 336, 338, and 340 is associated with a given parameter. Thus, if the first descriptive pulse 330 appears about 15 msec after the identification pulse 326, then the parameter associated with the first descriptive pulse 330 is considered normal or within prescribed tolerances. If, however, there is no pulse present at 15 ms after the identification pulse 326, then there is a problem with the parameter that requires further examination. Similarly, the second descriptive pulse 332 will be found, if at all, about 30 msec after the identification pulse 326 or 15 msec after the assigned slot for the first descriptive pulse 330. If the second descriptive pulse 332 is present, the parameter is considered normal. If the second descriptive pulse 332 is absent, then there is a problem with the measured parameter that requires further investigation. The third through sixth descriptive pulses (334, 336, 338, and 340) are similarly evaluated.

Alternatively, the pulse-number modulation technique can utilize the entire combination of descriptive pulses generated during the physiological refractory period. In other words, if there are a maximum of six descriptive pulses (i.e. 330, 332, 334, 336, 338, and 340) within the refractory period, and each descriptive pulse is either present or absent, then a total of 64 different combinations can result. Each distinct combination may be indicative of a different predefined condition of the pacemaker, as defined in an associated look-up table.

From the foregoing, it should be appreciated that the present invention thus provides a method for selectively producing a pulse-modulated EGM or ECG signal descriptive of pacemaker parametric information, with the pulse-modulated cardiac pacing signal being suitable for transtelephonic transmission to receivers located at remote locations.

A Representative Microprocessor-Based Pacemaker

Figure 8:
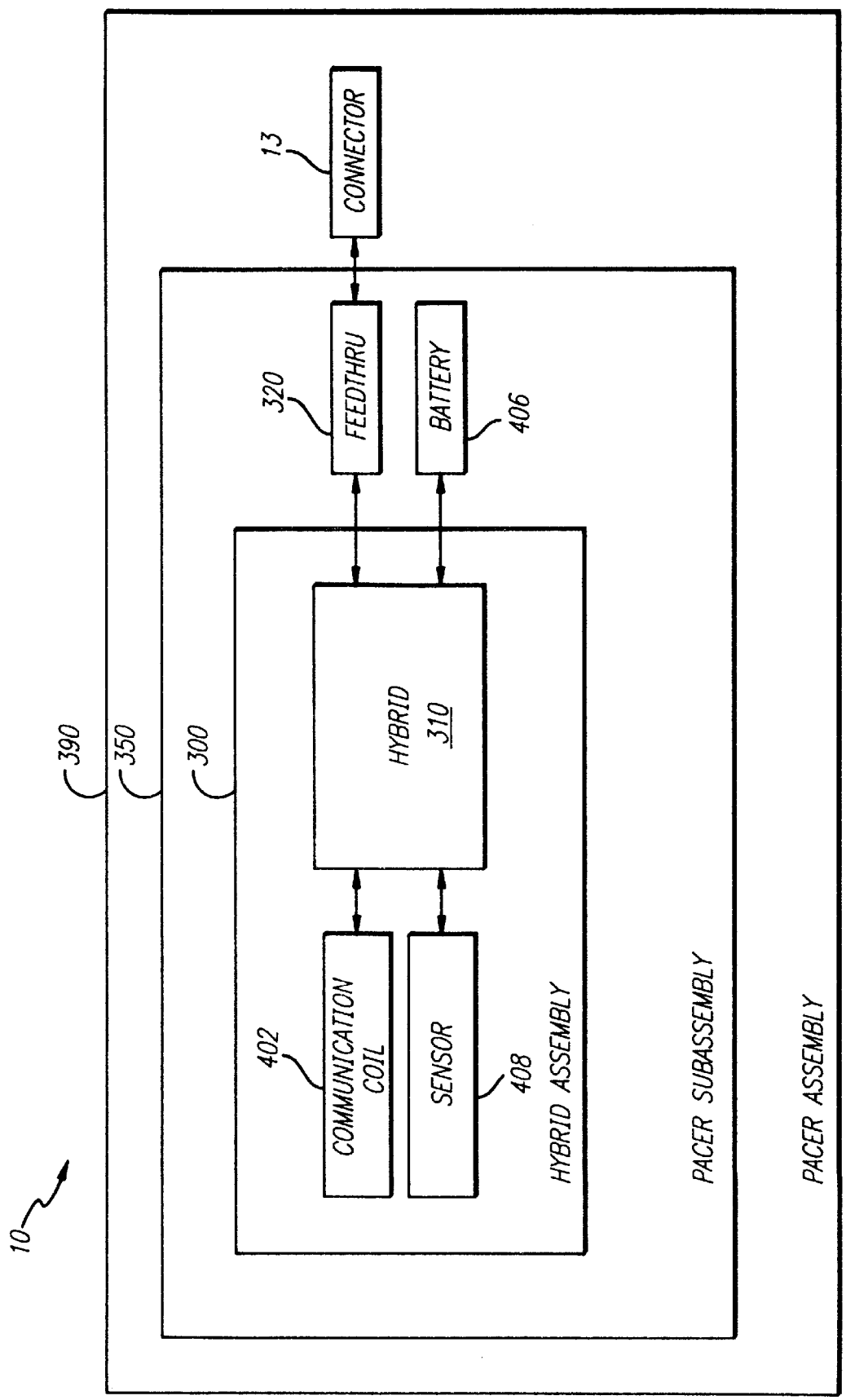
FIG. 8 is an assembly block diagram that depicts the various electrical/electronic hardware assemblies and subassemblies of an implantable pacemaker made in accordance with a microprocessor-based embodiment of the invention.

While the described invention may be carried out using any type of implantable pacemaker which can be programmed, or operated, to provide the ventricular pulse modulation in the manner described, one type of pacemaker that may be used with the present invention is a multi-mode rate-responsive microprocessor-based pacemaker of the kind depicted in FIGS. 8–11. FIG. 8 depicts a block diagram of the various hardware assemblies and subassemblies that may be used within such a multi-mode rate-responsive microprocessor-based pacemaker. As seen in FIG. 8, a pacemaker 10 is made up of a hybrid assembly 300, a pacer subassembly 350, and a pacer assembly 390. The hybrid assembly 300 includes almost all of the electronic circuitry and components of the pacemaker 10. Such circuitry and components include a communication coil 402, a sensor(s) 408 (which typically comprises a piezoelectric crystal used as an accelerometer), and a hybrid integrated circuit 310. The hybrid assembly 300 is combined with a battery 406 and feedthrough connectors 320 to form the pacer subassembly 350. All of the elements of the pacer subassembly 350 are housed in, or mounted to, a case 400 which is hermetically sealed. Electrical connection is made with the circuits sealed inside of the pacer subassembly 350 by way of the feedthru connectors 320. Such feedthru connectors 320 are then connected to the lead connector 13, attached to the pacer subassembly 350, in order to form the-completed pacer assembly 390. The completed pacer assembly 390, when suitable pacing/sensing leads 74 and 76 (FIG. 1) are attached thereto through the connector 73, forms a functional pacemaker.

Figure 9:
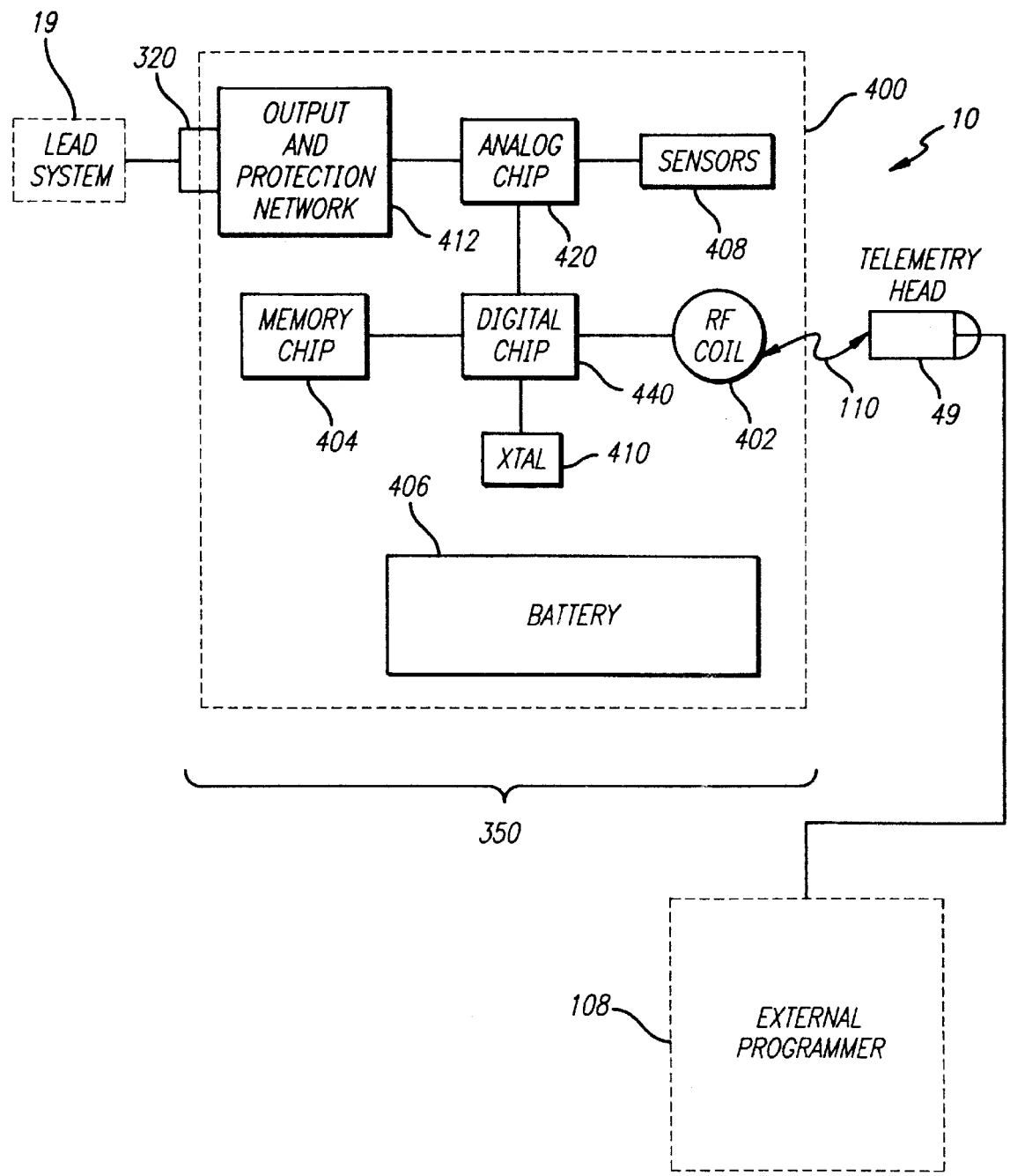
FIG. 9 is a block diagram of the hybrid assembly shown in FIG. 8.

Referring next to FIG. 9, a more detailed block diagram of the pacemaker 10, and particularly the pacer subassembly 350, is shown. As seen in FIG. 9, the pacemaker 10 and a lead system 19 (which lead system 19 comprises the leads 74 and 76, and the connector 73) are used with (i.e., programmed by and/or monitored with) the external programmer 108 (FIG. 1). The lead system 19 may also include an oxygen sensor lead, which lead contains a light emitting diode (LED) detector assembly used to measure the oxygen content of the blood. Such a lead is described, e.g., in U.S. Pat. No. 4,815,469, incorporated herein by reference.

The external programmer 108 includes a telemetry head 49 that is positioned proximate the implantable pacemaker 10 whenever a communication link 110 is to be established between the pacemaker 10 and the external programmer 108. Such telemetry head 49 may be used in conjunction with the invention in order to facilitate transfer of the EGM signal to a location external to the patient, where it can be downloaded transtelephonically to a remote location. Alternatively, conventional external electrodes may be used to sense the patient's ECG signal, which signal may then be send transtelephonically to the remote location. The external programmer, when used, may be of conventional design, as described, e.g., in U.S. Pat. No. 4,809,697, incorporated herein by reference.

The components of the pacer subassembly 350 are housed within a suitable sealed case or housing 400 (which case or housing is represented in FIG. 6 by the dashed line 400). The case 400 is preferably a 15 titanium metal case. The components within the case 400 include an RF coil 402, a memory chip 404, a battery 406, one or more physiological or other sensors in a sensor circuit 408, a crystal 410, an output/protection network 412, an analog chip 420 and a digital chip 440.

The battery 406, which is by volume the largest component within the pacer subassembly 350, may be of conventional design, and is generally a lithium battery that provides operating power to all of the electronic circuits within the pacer subassembly. The RF coil 402 is used to establish the communication link 110 with the telemetry head 49. The crystal 410 is used in conjunction with a crystal oscillator circuit on the digital chip 440 (described below) to provide a stable clock frequency for the pacemaker circuits. In the preferred embodiment, the frequency of the crystal oscillator is 32 KHz, although any suitable frequency could be used. The sensor circuit 408 includes appropriate sensors used by the pacemaker as it carries out a rate-responsive pacing function. For example, in one embodiment, the sensor circuit 408 includes an accelerometer adapted to sense patient activity.

The memory chip 404 may be any suitable type of memory device wherein data may be stored and retrieved. Preferably the memory chip 404 is a low-power static random access memory (SRAM) chip wherein the operating parameters, e.g., control variables, of the pacemaker may be stored, and wherein sensed data may be stored, as required. The analog chip 420 and the digital chip 440 contain the main processing and control circuits of the pacemaker. These chips are advantageously designed to minimize the number of components needed external thereto for operation of the pacemaker. The analog chip 420 interfaces with the lead system 19 through the output and protection network 412 and the feedthru connectors 320. The network 412 includes, e.g., output coupling capacitors and circuits which protect the analog chip 420 from high static or other voltages that might be coupled to the lead system 19, as are commonly used in implantable medical devices. The feedthru connectors 320 allow electrical connection through the hermetically sealed case 400, and may be of conventional design.

Figure 10:
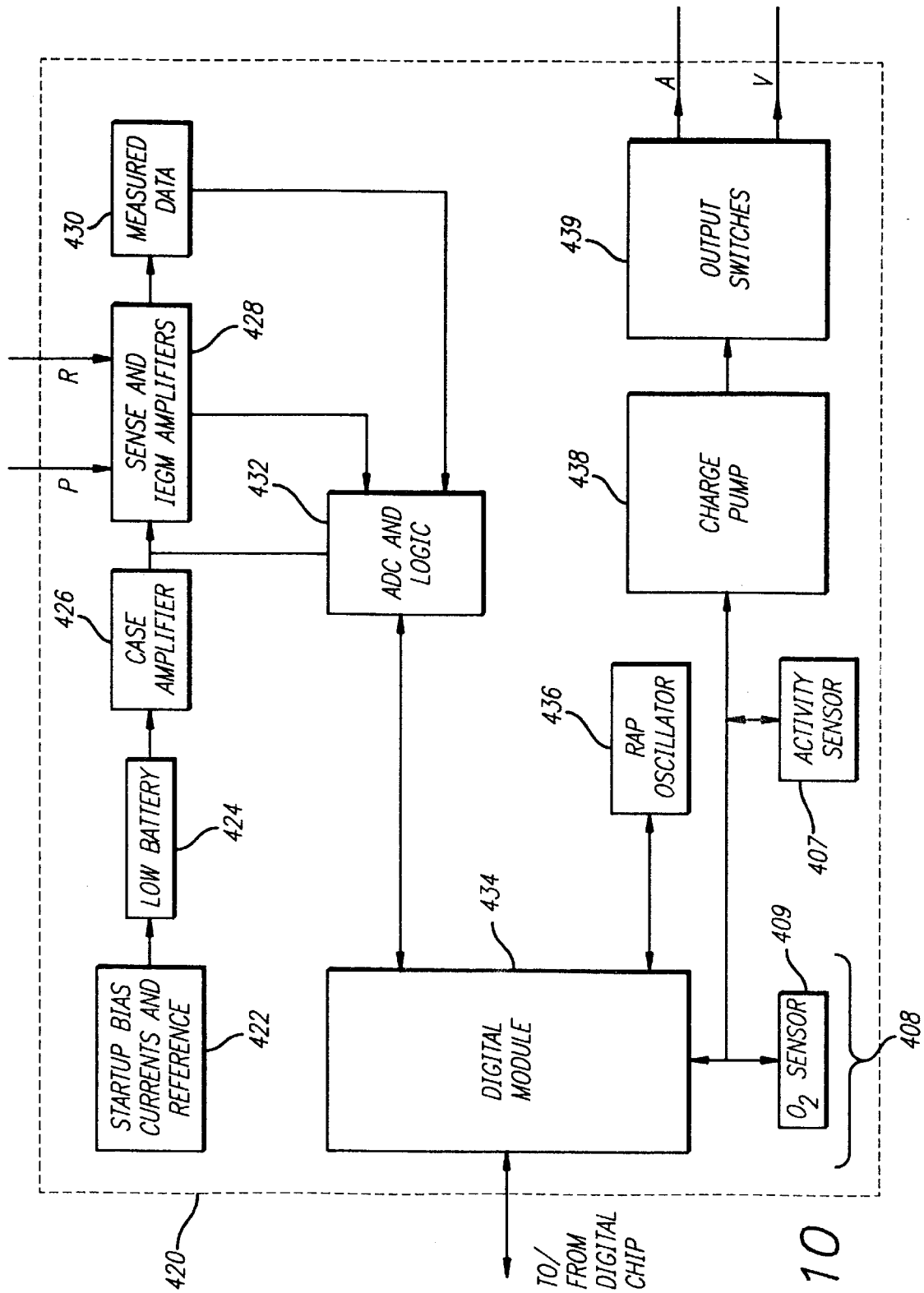
FIG. 10 is a block diagram of the analog chip portion of the hybrid assembly shown in FIG. 9.

Referring next to FIG. 10, a block diagram of the analog chip 420 is shown. The analog chip contains all the necessary sub-systems and modules to interface to the lead system 19 and the digital chip 440. For example, a startup/bias-current/reference module 422 contains the power-up signals used to initialize the pacer circuit when the battery is first applied. A low battery module 424 detects four voltage levels of the battery voltage for determining the battery status. A case amplifier 426 generates a CASE bias voltage that is used as a reference for the sense and IEGM (intracardiac electrogram) amplifier module 428. The sense and IEGM amplifier module 428 includes the P-wave amplifier 82 and the R-wave amplifier 84, described in FIG. 1. A measured data module 430 measures the battery voltage and current and other analog parameters of the pacing system. An ADC and Logic module 432 includes an analog-to-digital converter (ADC) and timing logic that are used to convert the analog signals of the pacemaker to 8-bit digital words. These digital words are then passed to a digital module 434, which module is used to generate all the basic timing and bus control functions as data is passed back and forth between the analog chip 420 and the digital chip 440.

Still referring to FIG. 10, it is seen that a Runaway Protection (RAP) circuit oscillator 436 is also coupled to the Digital Module 434. Such oscillator 436 provides an independent time base for limiting the highest pacing rate allowed by the pacemaker. Further coupled to the digital module 434 is the sensor network 408 (also referred to as the sensor circuit 408). The sensor network 408 includes appropriate sensors for sensing activity and other parameters. For example, an O2 sensor circuit 409 may be used in conjunction with the oxygen sensor lead, when used, to measure blood oxygen of the patient. An activity sensor 407 may also be used to sense patient activity as measured, e.g., by an accelerometer. A charge pump circuit 438 generates the output voltages for the stimulation pulses that are delivered to the patient's heart. A network of output switches 439 connects the charge developed by the pump circuit 438 to the output leads at the appropriate time to form the appropriate stimulation pulses.

It is thus seen that the analog chip 420 contains the necessary circuitry to sense and detect atrial or ventricular events, digitize IEGM WAVEFORMS, measured data and other various analog signals, and provide such sensed and digitized signals to the digital module 434 for use by the digital chip 440. The charge pump circuit 438 acts as a voltage doubler/tripler for high output pulse capability. The output pulse width is controlled by the output switches 439. The condition of the battery is monitored, and independent Runaway Protection is provided.

Figure 11:
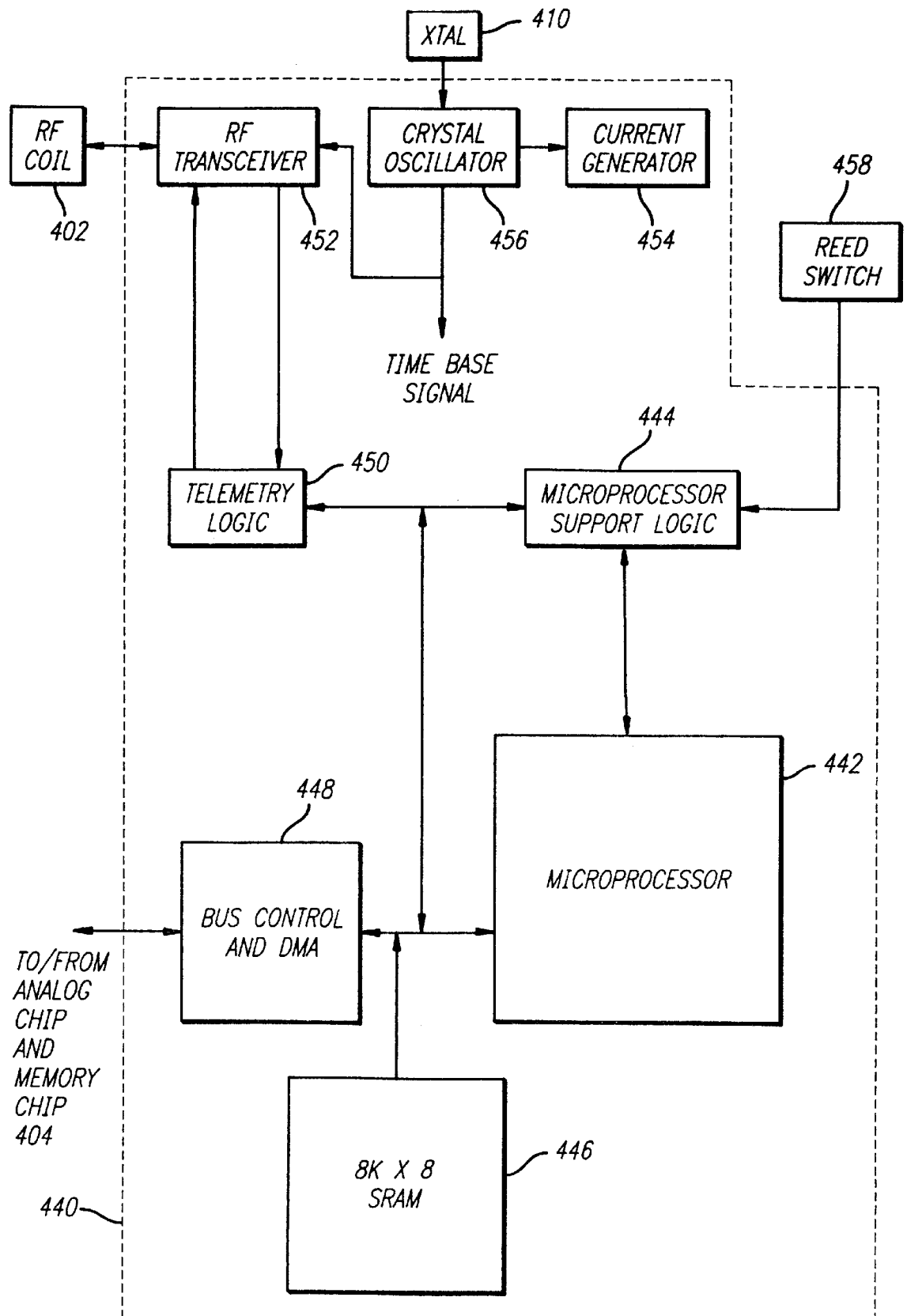
FIG. 11 is a block diagram of the digital chip portion of the hybrid assembly shown in FIG. 9, and illustrates the use of a microprocessor to control the operation of the pacemaker.

Turning next to FIG. 11, a diagram of the digital chip 440 is shown. As seen in FIG. 11, the main control element of the pacemaker is a microprocessor 442, which microprocessor is included as the main component on the digital chip 440. The digital chip 440 contains all the necessary logic to interface the analog chip 420 with the microprocessor 442. The microprocessor 442 includes a basic CPU (central processing unit). In addition, an 8K by 8 static random access memory (SRAM) 446, or equivalent memory element, is connected to the microprocessor 442 to store data and programs. Microprocessor support logic 444, also coupled to the microprocessor 442, includes interrupt logic, timer logic, noise/sensed event logic, and magnet status logic. A bus controller 448 is further included on the digital chip 440 to provide direct memory access (DMA) timing and control of data transfer with the analog chip 420, and the memory chip 404, including timing and control of the analog-to-digital converter 432 (FIG. 13) and telemetry data. Telemetry logic 450 contains clock logic, IEGM and marker logic, telemetry command protocol logic, telemetry interrupt logic, error checking logic and CPU reset logic. An RF transceiver 452, coupled to the RF coil 402, transmits and receives telemetry data from the external programmer 108 through the telemetry head 49 (see FIG. 6). A crystal oscillator circuit 456, in conjunction with the crystal 410 (external to the digital chip 440) provides a crystal-controlled time base signal for the pacemaker system. A current generator 454 provides the bias currents for the digital chip. A reed switch 458 (external to the digital chip 440) is coupled to the microprocessor support logic 444. The reed switch 458 detects the presence of a magnetic field, which magnetic field is present whenever the telemetry head 49 (FIG. 6) is in place on the patient's skin above the location where the pacemaker is implanted.

The pacemaker architecture and circuitry described in connection with FIGS. 8–11 provides the basic functions of the pacemaker described in connection with FIG. 1, plus other pacing/sensing functions as are known in the art. For purposes of the present invention, the pacemaker circuitry of FIGS. 8–11 stores the type of modulation to be used, regularly monitors the parameters that are to be included in the selected modulation, monitors the magnet detection circuitry for the appropriate patient-initiated trigger which starts the modulation sequence, and then generates the appropriate sequence of ventricular stimulation pulses, e.g., as shown in FIGS. 3 or 5, having the appropriate time intervals between each pulse (or having other defined modulation characteristics) in order to convey the specified patient/parameter information. Such time intervals or segments then convey the specified information as part of the resulting EGM/ECG signal, in the manner depicted, e.g., in the tables of FIG. 4 or FIG. 6.

While the invention herein disclosed has been described by means of specific embodiments and applications thereof, numerous modifications and variations could be made thereto by those skilled in the art without departing from the scope of the invention set forth in the claims.

What is claimed is:

1. In an implantable cardiac pacemaker including means for generating ventricular stimulation pulses, a method of selectively pulse-modulating a predetermined number of the ventricular stimulation pulses with descriptive pacemaker parametric information, said pulse-modulated ventricular stimulation pulses being applied to a patient's heart to produce a pulse-modulated cardiac signal suitable for transtelephonic transmission to a receiver located at a remote location, the method comprising the steps of:

(a) ascertaining parametric information for a plurality of parameters;
    (b) varying pulse characteristics of said predetermined number of ventricular stimulation pulses to be descriptive of said parametric information for the plurality of parameters; and
    (c) delivering to a patient's heart said predetermined number of ventricular stimulation pulses having said descriptive pulse characteristics, said predetermined number of ventricular stimulation pulses further having sufficient energy to cause captured;

whereby the cardiac signal is pulse-modulated by said predetermined number of ventricular stimulation pulses to contain said descriptive parametric information.

2. The method, as set forth in claim 1, wherein the step of varying said pulse characteristics comprises varying the timing interval between said predetermined number of ventricular stimulation pulses to be descriptive of said parametric information for said plurality of parameters.

3. The method, as set forth in claim 2, further comprising an initial step of initializing a pulse modulation routine, said initializing step further including the steps of:

(i) defining the plurality of parameters to include parameters that relate to at least one of the status of the pacemaker operation and the status of patient's condition;
    (ii) defining a pulse modulation sequence, said pulse modulation sequence including a predetermined number of descriptive pulse segments, each of said descriptive pulse segments being characterized by the occurrence of two successive ventricular stimulation pulses;
    (iii) associating each parameter with one of said descriptive pulse segments; and
    (iv) defining prescribed timing intervals for each of said descriptive pulse segments that are descriptive of said parametric information for said associated parameters.

4. The method, as set forth in claim 3, wherein the step of defining said pulse modulation sequence further comprises:

defining said pulse modulation sequence to include a pair of identification pulse segment followed by the predetermined number of descriptive pulse segments, said descriptive pulse segments having said prescribed timing intervals that are descriptive of said parametric information for said plurality of parameters.

5. The method, as set forth in claim 3, wherein the step of defining said pulse modulation sequence further comprises defining said pulse modulation sequence to include an identification pulse segment followed by six descriptive pulse segments, said descriptive pulse segments having said prescribed timing intervals that are descriptive of said parametric information for said measured parameters.

6. The method, as set forth in claim 2, wherein the step of generating said predetermined number of ventricular stimulation pulses further comprises:

generating a pair of identification pulses followed by the predetermined number of descriptive pulses having timing intervals between pulses that are descriptive of said parametric information for said plurality of parameters.

7. The method, as set forth in claim 6, wherein the step of generating a plurality of ventricular stimulation pulses further comprises generating a pair of identification pulses followed by six descriptive pulses wherein said timing intervals between pulses are descriptive of said parametric information for a respective parameter.

8. The method, as set forth in claim 6, wherein said timing intervals between successive descriptive pulses are of a duration that is sufficient to ensure overdrive pacing.

9. The method, as set forth in claim 6, wherein said timing intervals between successive descriptive pulses range in duration from about 500 ms to about 700 ms.

10. The method, as set forth in claim 2, wherein the step of varying said timing intervals between said plurality of ventricular stimulation pulses further comprises the step of:

setting said timing intervals between each of said plurality of ventricular stimulation pulses to prescribed values wherein each combination of prescribed values is indicative of said parametric information for a respective parameter.

11. The method, as set forth in claim 1, further comprising the step of initially triggering said implantable pacemaker to perform steps (a) through (c) above by placing a magnet over said pacemaker.

12. The method, as set forth in claim 1, further comprising the steps of:

recording said pulse-modulated cardiac signal and transtelephonically transmitting said recorded pulse-modulated cardiac signal to a remote location.

13. The method, as set forth in claim 12, further comprising the step of:

receiving and analyzing said transmitted, pulse-modulated cardiac signal to extract said parametric information contained therein.

14. The method, as set forth in claim 1, wherein the step of defining said measured parameters further includes defining a measured parameter indicative of the status of a battery in said implantable pacemakers.

15. The method, as set forth in claim 1, wherein the ascertaining step further includes ascertaining a parameter indicative of the status of an atrial lead coupled to said implantable pacemaker.

16. The method, as set forth in claim 1, wherein the ascertaining step further includes ascertaining a parameter indicative of the status of a ventricular lead coupled to said implantable pacemaker.

17. The method, as set forth in claim 1, wherein the ascertaining step further includes ascertaining a parameter indicative of the status of a sensor coupled to said implantable pacemaker.

18. The method, as set forth in claim 1, wherein the step of defining said measured parameters further includes defining a measured parameter indicative of extrsystoles rate of the patient.

19. The method, as set forth in claim 1, wherein the step of defining said measured parameters further includes defining a measured parameter indicative of arrhythmic conditions of the patient.

20. A cardiac pacing system that selectively provides a pulse-modulated cardiac pacing signal descriptive of pacemaker parametric information, said pulse-modulated cardiac pacing signal being suitable for transtelephonic transmission to a receiver located at a remote location, the cardiac pacing system comprising:

an implantable pacemaker, said pacemaker including means for generating ventricular stimulation pulses having sufficient energy to cause capture; and processing means for controlling the operation of said pacemaker, said processing means including:
means for defining a plurality of parameters;
means for ascertaining parametric information for said plurality of parameters;
means for triggering the generation of a sequence of a plurality of ventricular stimulation pulses;
means for varying pulse characteristics of the sequence of plurality of ventricular stimulation pulses wherein said pulse characteristics are descriptive of said parametric information for said plurality of parameters so that a patient's cardiac signal is pulse-modulated with said parametric information.

21. The cardiac pacing system of claim 20, wherein said means for varying said pulse characteristics of said plurality of ventricular stimulation pulses further comprises means for varying timing intervals between said plurality of ventricular stimulation pulses to be descriptive of said parametric information for said plurality of parameters.

22. The cardiac pacing system of claim 21, wherein said plurality of ventricular stimulation pulses further comprises at least one identification pulses followed by the sequence of descriptive pulses, said descriptive pulses having timing intervals that are descriptive of said parametric information for said plurality of parameters.

23. The cardiac pacing system of claim 21, wherein said means for varying timing intervals between said plurality of ventricular stimulation pulses to be descriptive of said parametric information for said plurality of parameters further comprises:

(i) means for defining a plurality of descriptive pulse segments, each of said descriptive pulse segments characterized by the occurrence of two successive ventricular stimulation pulses from said plurality of ventricular stimulation pulses;

(ii) means for associating each of the plurality of parameters with one of said descriptive pulse segments; and (iii) means for varying the timing interval of each of said descriptive pulse segments to be indicative of said parametric information for said associated parameter.

24. The cardiac pacing system of claim 21, wherein said means for varying said timing intervals between said plurality of ventricular stimulation pulses further includes means for setting said timing intervals between each of said plurality of ventricular stimulation pulses to prescribed values such that each combination of prescribed values is indicative of the parametric information for said associated parameter.

25. The cardiac pacing system of claim 20, further comprising:

means for recording said pulse-modulated cardiac pacing signal; and means for transtelephonically transmitting said recorded signal to a remote location.

26. The cardiac pacing system of claim 25, further comprising means for receiving and analyzing said pulse-modulated signal to extract said parametric information contained therein.

27. A cardiac stimulation device that selectively provides a cardiac pacing signal encoded with descriptive operational information, comprising:

pulse generating means for generating ventricular stimulation pulses having sufficient energy to cause capture; and processing means for pulse-modulating the ventricular stimulation pulses with descriptive operational information, the processing means including:
means for determining descriptive information for a plurality of operational conditions;
means for triggering a sequence of ventricular stimulation pulses;
means for pulse-modulating the sequence of ventricular stimulation pulses, wherein each of the modulated pulses contain the descriptive information of a corresponding operational condition; and
means for applying the sequence of pulse-modulated ventricular stimulation pulses to a patient's heart so that the cardiac signal has the descriptive information encoded therein.

28. The cardiac stimulation device of claim 27, wherein the pulse-modulating means comprises:

means for varying timing intervals between the plurality of ventricular stimulation pulses.

29. The cardiac stimulation device of claim 27, wherein the pulse-modulating means comprises:

means for varying pulse amplitude between the plurality of ventricular stimulation pulses.

30. The cardiac stimulation device of claim 27, wherein the pulse-modulating means comprises:

means for varying pulse width between the plurality of ventricular stimulation pulses.

31. The cardiac stimulation device of claim 27, wherein the pulse-modulating means comprises:

means for varying pulse number between the plurality of ventricular stimulation pulses.

32. The cardiac stimulation device of claim 27, further comprising:

means for transtelephonically transmitting the pulse-modulated cardiac signal to a remote location.

33. The cardiac stimulation device of claim 27, wherein the plurality of operating conditions includes the status of a battery.

34. The cardiac stimulation device of claim 27, wherein the plurality of operating conditions includes the status of an atrial lead coupled to the cardiac stimulation device.

35. The cardiac stimulation device of claim 27, wherein the plurality of operating conditions includes the status of an ventricular lead coupled to the cardiac stimulation device.

36. The cardiac stimulation device of claim 27, wherein the plurality of operating conditions includes the status of a sensor coupled to the cardiac stimulation device.

37. The cardiac stimulation device of claim 27, wherein the plurality of operating conditions includes an extrasystoles rate of the patient.

38. The cardiac stimulation device of claim 27, wherein the plurality of operating conditions includes the status of a patient's arrhythmic condition.

* * * * *